United States Patent
Dinarello et al.

(10) Patent No.: US 9,522,179 B2
(45) Date of Patent: Dec. 20, 2016

(54) COMPOSITIONS AND METHODS FOR MODULATING CARDIAC CONDITIONS

(75) Inventors: Charles A. Dinarello, Boulder, CO (US); Antonio Abbate, Glen Allen, VA (US); Eli C. Lewis, Be'er Sheva (IL)

(73) Assignees: VIRGINIA COMMONWEALTH UNIVERSITY, Richmond, VA (US); THE REGENTS OF THE UNIVERSITY OF COLORADO, Denver, CO (US)

(*) Notice: Subject to any disclaimer, the term of this patent is extended or adjusted under 35 U.S.C. 154(b) by 659 days.

(21) Appl. No.: 13/582,724

(22) PCT Filed: Mar. 4, 2011

(86) PCT No.: PCT/US2011/027283
§ 371 (c)(1),
(2), (4) Date: Apr. 19, 2013

(87) PCT Pub. No.: WO2011/109768
PCT Pub. Date: Sep. 9, 2011

(65) Prior Publication Data
US 2013/0195859 A1    Aug. 1, 2013

Related U.S. Application Data

(60) Provisional application No. 61/310,645, filed on Mar. 4, 2010, provisional application No. 61/312,589, filed on Mar. 10, 2010.

(51) Int. Cl.
*A61K 39/00* (2006.01)
*A61K 38/57* (2006.01)

(52) U.S. Cl.
CPC ..................................... *A61K 38/57* (2013.01)

(58) Field of Classification Search
None
See application file for complete search history.

(56) References Cited

U.S. PATENT DOCUMENTS 6,924,267 B2 *  8/2005  Daemen et al. ............. 514/14.9
7,704,958 B1    4/2010  Shapiro

FOREIGN PATENT DOCUMENTS

| EP | 0511188 A2 * | 10/1992 |
| WO | WO 00/51624 A1 * | 9/2000 |
| WO | WO 0051624 A2 * | 9/2000 |
| WO | WO 2008/033890 A2 * | 3/2008 |

OTHER PUBLICATIONS

International Search Report, Written Opinion issued in PCT/US2011/027283 mailed on Oct. 14, 2011, 4 pages.

* cited by examiner

*Primary Examiner* — Michael Szperka
(74) *Attorney, Agent, or Firm* — Faegre Baker Daniels LLP

(57) ABSTRACT

Embodiments herein report methods and compositions for treating cardiac conditions. In certain embodiments, compositions and methods relate to reducing, inhibiting or treating a subject having or suspected of undergoing cardiac remodeling after a cardiac event. Other embodiments herein relate to compounds including naturally occurring and synthetic compositions of alpha-1 antitrypsin and fragments thereof.

20 Claims, 8 Drawing Sheets

COMPOSITIONS AND METHODS FOR MODULATING CARDIAC CONDITIONS

CROSS REFERENCE TO RELATED APPLICATIONS

This application claims the benefit of PCT application No. PCT/US2011/027283 filed 4 Mar. 2011, which claims the benefit of U.S. Provisional Application No. 61/310,645, filed on 4 Mar. 2010, and U.S. Provisional Application No. 61/312,589, filed on 10 Mar. 2010, which are incorporated herein by reference in their entirety for all purposes.

FEDERALLY FUNDED RESEARCH

This invention was made with government support under grant number AI015614 awarded by The National Institutes of Health. The government has certain rights in the invention.

The studies disclosed herein were supported in part by the American Heart Association Beginning Grant-in-Aid (Mid-Atlantic Affiliate), NIH Grant AI-15614 and Juvenile Diabetes Research Foundation Grant 2-2007-103. The U.S. government has certain rights to practice the subject invention.

FIELD

Embodiments herein relate to compositions, methods and uses for alpha-1 antitrypsin ($\alpha$-1 antitrypsin, AAT) or derivative or analog or peptide or mutant thereof for treating a cardiac condition in a subject. In certain embodiments, AAT or derivative thereof or analog thereof may be used to modulate remodeling in a subject having a myocardial infarction or other heart condition. In other embodiments, AAT or derivative thereof or analog thereof can be used for treating a subject having a heart condition that can lead to remodeling of the heart tissue.

BACKGROUND

AAT

Normal plasma concentration of alpha-1 antitrypsin (AAT) ranges from 1.3 to 3.5 mg/ml. Under certain conditions, AAT easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen.

Cardiac Remodeling

Ventricular remodeling (or cardiac remodelling) includes changes in size, shape, and function of the heart after injury to the ventricles. The injury is often due to acute myocardial infarction (for example, transmural or ST segment elevation infarction), but can be from a number of causes that result in increased pressure or volume overload (forms of strain) on the heart.

SUMMARY

Embodiments herein provide for methods and compositions for treating a subject having a cardiac event. In certain embodiments, compositions and methods concern modulating recovery of a subject having had a cardiac event. In some embodiments, a cardiac event can be a myocardial infarction, myocardial ischemia, chronic systemic arterial and venous hypertension and pulmonary arterial and venous hypertension, congenital heart disease with and without intracardiac shunting, valvular heart disease, idiopathic dilated cardiomyopathy, infectious and non-infectious myocarditis, stress cardiomyopathy (as seen associated with critical care illnesses, physical and emotional stress, and intracranial hemorrhage and stroke), septic cardiomyopathy, atrial and ventricular arrhythmias, cardioplegia, cardiac arrest, or other event that damages heart muscle. In accordance with these embodiments, damage to heart muscle can lead to decline in the functioning myocytes and reduction in the pumping or filling ability of the heart.

Some embodiments of the present invention report modulating the onset or progression of cardiac tissue remodeling (e.g. enlargement and necrosis of cardiac tissue), for example, left or right ventricular (LV) remodeling. In accordance with these embodiments, intervention for example, by administering a composition disclosed herein, can modulate onset, severity (e.g of damage) or progression before, during, or after a cardiac event that can lead to heart muscle damage. In yet other embodiment, compositions disclosed herein can be administered to a subject having a heart condition to reduce early or late infarct size. In accordance with these embodiments, an early infarct can be one measured before (for example, a baseline), during or within 48 hours after surgery or other cardiac event. In other embodiments, a late infarct can be one measured after 48 hours or up to days or weeks after surgery or other cardiac event, for example 7 days after a cardiac event. In yet other embodiments, compositions disclosed herein can be used to treat a subject having a cardiac event (e.g. myocardial infarction), to modulate cardiac enlargement and dysfunction as a consequence of the cardiac event by about 5%, or about 10%, or about 15%, or about 20% or about 25%, or about 30% or more compared to a subject not treated with these compositions.

Certain embodiments concern compositions for treating a subject having a cardiac event. In accordance with these embodiments, a composition can include, naturally occurring alpha-1 antitrypsin (e.g. human), or fragments, or derivatives thereof, or recombinants, or mutants thereof having no significant serine protease inhibitor activity, or alleles thereof (for example, there are approximately 100 naturally occurring AAT variants), or analogs thereof or fusion protein thereof (e.g. a human IgG or fragment of human IgG). Some embodiments concern administering naturally occurring AAT to a subject having or having had a cardiac event in order to modulate LV remodeling. Other embodiments can concern administering a composition of one or more carboxyterminal derivative(s) or fragment(s) of AAT including, for example, a fragment of the last 80 AAs of the molecule to a subject.

In other embodiments, compositions disclosed herein can be used to modulate production or activity of caspase-1 or other factors, for example, interleukin-6, interleukin-17 and monocyte chemoattractant protein-1 (MCP-1) in a subject having suffered a cardiac event, for example a heart attack. In certain embodiments, compositions administered to a subject having such a condition can modulate atherosclerosis in the subject. In some embodiments, compositions described herein can be used for inhibiting caspase-1 activities related to a cardiac event Inhibition of caspase-1 activity can reduce processing of IL-1β and IL-18, reduce infiltration of myeloid cells and necrosis of tissue-related to the cardiac event.

Compositions contemplated herein may further include an agent selected from the group consisting of a cardiac condition treatment and/or prevention agent, an anti-inflammatory agent, an immunosuppressive agent, an immunomodulatory agent, an anti-viral agent, an anti-pathogenic agent, an anti-bacterial agent, a protease inhibitor, and a combination thereof. Any agent of use to treat a subject having a cardiac event can be combined with compositions disclosed herein for reduced remodeling or reduced infarction size.

In certain embodiments, compositions and methods disclosed herein can be used to reduce or prevent LV remodeling in a subject. In accordance with these embodiments, reduction in LV remodeling in a subject having or having had a cardiac event can be on the order of about 10-20%, or about 30-40%, or about 50-60%, or about 75-100% reduction or inhibition. For example, left ventrical end-diastolic diameters (LVEDD) and left ventrical end-systolic diameters (LVESD) can be reduced in a subject undergoing remodeling post-cardiac event compared to a subject not receiving at least one of the composition disclosed herein.

In certain embodiments, pharmaceutical compositions herein can be administered orally, systemically, via an implant (e.g. coronary stent or catheter), time released or slow-release compositions (e.g. gel, microparticles etc.), intravenously, topically, intrathecally, intracranially, intravaginally, intraventricularly, intranasally such as inhalation, subcutaneously, or by other means known in the art or a combination thereof.

In certain embodiments, α1-antitrypsin used in the methods and compositions herein can include, but is not limited to, naturally occurring AAT (a 394 AA protein that makes up about 90% of AAT derived from platelets), Aralast™ (Baxter), Zemaira™ (Aventis Behring), Prolastin™ (Bayer), Aprotonin™ or Trasylol™ (Bayer Pharmaceutical Corporation) and Ulinistatin™ (Ono Pharmaceuticals, Inc.), Kamada AAT (Kamada, Inc., Israel) or any combination thereof. In other embodiments, AAT or an AAT fragment or an AAT analog used in methods and compositions herein can include naturally occurring AAT (e.g. isolated from mammalian blood) or AAT fragment or analog or allele thereof.

In certain embodiments, compositions for administration can be in a range of between about 10 ng and about 10 mg per ml or mg of the formulation. A therapeutically effective amount of AAT peptides or drugs that have similar activities as AAT or peptides drug may be measured in molar concentrations and may range between about 1 nM and about 10 mM. The formulation is also contemplated in combination with a pharmaceutically or cosmetically acceptable carrier. Precise doses can be established by well known routine clinical trials without undue experimentation. In one embodiment, a subject may be treated for a cardiac event with a single dose (e.g 60 mg/kg to 80 mg/kg by IV infusion) of an active agent (e.g. AAT or fragment thereof or mutant thereof). In accordance with this embodiment, the subject can be treated with follow-on treatments (e.g. 5 to 10 days following a single dose) as determined by a health professional. Other embodiments can include using a control population having a placebo (e.g. human serum albumin administration or other comparable placebo). In some embodiments, compositions disclosed herein can range from about 30 to about 150 mg/kg in single or in multiple doses to a subject. In other embodiments, a composition disclosed herein can be administered to a subject every 24 hours at reperfusion.

In certain embodiments, the subject is a mammal. In some embodiments, the mammal is a human. In other embodiments, the subject is a pet, a domesticated animal or livestock.

In other embodiments, the subject or mammal can be a domesticated or a non-domesticated mammal.

In certain embodiments, synthetic and/or naturally occurring peptides may be used in compositions and methods herein for example, providing other than serine protease inhibitor activity of AAT. Homologues, natural peptides derivatives, with sequence homologies to AAT including peptides directly derived from cleavage of AAT may be used or other peptides such as, peptides that have AAT-like activity other than serine protease inhibitor activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances can include, but are not limited to, certain phenylenedialkanoate esters, CE-2072, UT-77, and triazole peptoids. Examples of analogues are TLCK (tosyl-L-lysine chloromethyl ketone) or TPCK (tosyl-L-phenylalanine chloromethyl ketone) or any combination thereof.

In certain embodiments, compositions comprising human AAT mutants can be generated having no significant serine protease inhibitor activity of use in methods described herein (e.g AAT peptide derivative, or AAT mutant) In other embodiments, constructs of human AAT mutants having no significant serine protease activity can be associated with a vector. Other embodiments concern AAT-derived fragment constructs adapted to have no significant serine protease inhibitor activity.

In certain embodiments of the present invention, an anti-inflammatory agents or immunomodulatory agents can be included in any of the compositions disclosed. These agents include, but are not limited to, one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

In certain embodiments, synthetic and/or naturally occurring peptides may be used in compositions and methods disclosed in embodiments herein. Homologues, natural peptides, derived from AAT including peptides directly derived from cleavage of AAT may be used or other peptides such as, peptides that inhibit serine proteases or have AAT-like activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances comprising certain phenylenedialkanoate esters, CE-2072, UT-77, and triazole peptoids may be used. Examples of analogues are TLCK (tosyl-L-lysine chloromethyl ketone) or TPCK (tosyl-L-phenylalanine chloromethyl ketone).

Other embodiments concern combination therapies for the treatment of a subject having a cardiac event, for example a composition disclosed herein can be combined with any other agent known to prevent or reduce cardiac remodeling or treat other aspects of the cardiac event in the subject.

In some embodiments, AAT peptides contemplated for use in the compositions and methods of the present invention are also intended to include any and all of those specific AAT peptides including, but not limited to, 5 or 10 amino acid AAT derived peptides of SEQ ID NO:1. Any combination of consecutive amino acids depicting a portion of the carboxy terminus of AAT, such as consecutive amino acid sequences derived from SEQ ID NO:1. In addition, AAT variants are contemplated of use herein. A composition herein can include, but is not limited to a carboxy-terminal peptide or amino-terminal peptides corresponding to AAT, an analog thereof, any derivative of AAT carboxy terminus that binds to serpin-enzyme complex (SEC) receptor or a combination thereof.

Other embodiments concern methods of treatment for preventing or reducing cardiac remodeling in a subject in need of such a treatment, methods can include, but are not limited to, administering to the subject a composition having AAT, a mutant AAT construct or other AAT derived molecule (e.g. a peptide derivative, last 80 amino acids of AAT's carboxy terminus) and a pharmaceutically acceptable carrier to a subject. Any composition disclosed herein can be administered to the subject before, during, and/or after a cardiac event in the subject, for example, to modulate cardiac remodeling in the subject. In accordance with these embodiments, a subject having an acute heart event can be administered a composition disclosed herein to modulate remodeling of the heart. In certain embodiments, treating the subject with the composition modulate remodeling by at least 10%, or by at least 20% or by at least 30%, or by at least 40%, or by at least 50%, or by at least 60%, or by at least 70%, or by at least 80%, or by at least 90% compared to a subject not treated with the composition.

Other embodiments herein include treating myocardial infarction in a subject by identifying a subject having or a myocardial infarction; administering a therapeutically effective amount of a composition comprising AAT, AAT derivative having no significant serine protease inhibitor activity, AAT-like compound, AAT analog, AAT derivative, one or more peptides derived from AAT, any derivative or fragment of AAT carboxy terminus having no significant serine protease inhibitor activity or combination thereof to the subject. Administering the composition can include administering the composition directly to the organ (e.g heart or coronary artery) or other delivery methods such as intravenously or subcutaneously or via a catheter. It is contemplated herein that any know delivery device of use to treat a subject having a cardiac event is contemplated.

As such, those skilled in the art will appreciate that the conception, upon which this disclosure is based, can readily be used as a basis for designing other methods for carrying out the several features and advantages of embodiments of the present invention.

BRIEF DESCRIPTION OF THE DRAWINGS

The following drawings form part of the present specification and are included to further demonstrate certain embodiments disclosed herein. Embodiments may be better understood by reference to one or more of these drawings in combination with the detailed description of specific embodiments presented herein.

DESCRIPTION OF ILLUSTRATIVE EMBODIMENTS

Definitions

Figures 1A, 1B, 1C, 1D:
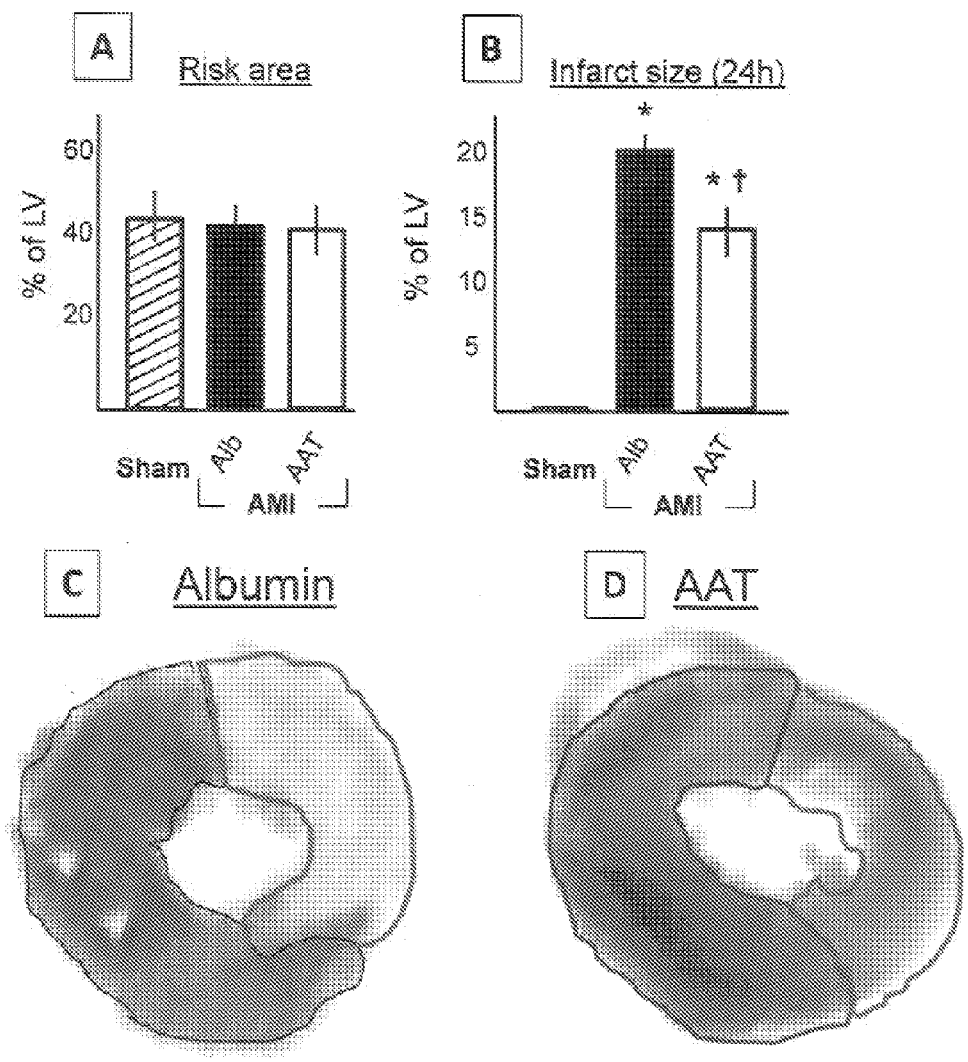
FIGS. 1A-1D represent analysis of risk area of a cardiac event and infarct size in the presence or absence of compositions of some embodiments reported herein. (A) and (B) represent histogram plots of percent of heart area in the presence or absence of compositions disclosed herein. (C) and (D) represent schematics of affected regions of a heart in the presence or absence of compositions disclosed herein.

As used herein, "a" or "an" may mean one or more than one of an item.

As used herein, "about" can mean plus or minus 10%, for example, about 10 minutes can mean from 9 to 11 minutes.

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

Acute myocardial infarction (AMI) can be characterized by an intense response after myocardial ischemia-reperfusion injury. Myocardial infarction (MI) or acute myocardial infarction (AMI), often referred to as a heart attack, is the interruption of blood supply to part of the heart that can cause some heart cells to necrose. Here, occlusion (blockage) of a coronary artery following rupture of a vulnerable atherosclerotic plaque can occur, which is an unstable collection of lipids (fatty acids) and white blood cells (e.g. macrophages) in the wall of an artery. Ischemia (restriction in blood supply) and oxygen shortage occurs and if left untreated for a sufficient period of time, can cause damage or death (infarction) of heart muscle tissue (myocardium).

Ventricular remodeling (or cardiac remodelling) can refer to changes in size, shape, and function of the heart after injury to the myocardium, endocardium, pericardium or valvular structures. Injuries can be due to acute myocardial infarction (usually transmural or ST segment elevation infarction), but may be from a number of causes that result in increased pressure or volume overload (forms of strain) on the heart. A cardiac event disclosed herein can be myocardial ischemia, chronic systemic arterial and venous hypertension and pulmonary arterial and venous hypertension, congenital heart disease with and without intracardiac shunting, valvular heart disease, idiopathic dilated cardiomyopathy, infectious and non-infectious myocarditis, endocarditis or pericarditis, stress cardiomyopathy (as seen associated with critical care illnesses, physical and emotional stress, and intracranial hemorrhage and stroke) and septic cardiomyopathy or other event that damages heart muscle. In some embodiments disclosed herein, after a cardiac insult or event occurs, a series of histopathological and structural changes can occur in the left ventricular myocardium that lead to progressive decline in left ventricular performance. Ultimately, ventricular remodeling can result in diminished contractile (systolic) function and reduced stroke volume. Ventricular remodeling can imply a decline in function (even though the word "remodeling" usually implies improvement). The term "reverse remodeling" in cardiology can imply an improvement in ventricular mechanics and function after a remote injury. Concentric hypertrophy can be due to pressure overload, while eccentric hypertrophy can be due to volume overload.

Cardiac myocyte is a major cell involved in remodeling. In addition, fibroblasts, collagen, the interstitium, and the coronary vessels play a role in remodeling. One scenario for remodeling is after myocardial infarction. Here, there is myocardial necrosis and random or disproportionate thinning of the heart. Thin, weakened areas can be unable to withstand the pressure and volume load on the heart in the same manner as the other healthy tissue. Therefore, dilatation of the chamber arising from the infarct region can occur. The initial remodeling phase after a myocardial infarction can lead to repair of the necrotic area and myocardial scarring that may, in some cases, be considered beneficial since there is an improvement in or maintenance of LV function and cardiac output. Over time, as the heart undergoes ongoing remodeling, the heart becomes less elliptical and more spherical and less functional. This repeated remodeling can lead to ventricular mass and volume increase, which can adversely affect cardiac function. In certain cases, diastolic function may become impaired, causing further decline. In certain embodiments, compositions described herein can be provided to a subject having a cardiac event wherein the composition modulates (e.g. reduces) effects related to cardiac myocytes.

Embodiments herein provide for methods and compositions for treating a subject having a cardiac disorder or event referred to above. In accordance with these embodiments, the composition may include, but is not limited to, alpha-1 antitrypsin, a carboxyterminal peptide derived therefrom (e.g. a carboxyterminal peptide of AAT found in the last 80 amino acids of AAT), an analog thereof, or fusion molecule thereof. In some embodiments, exogenous human derived AAT (e.g. wholly or partially purified from human blood) can be used to reduce ventricular remodeling and modulate cardiac function before, during or after a cardiac event. In other embodiments, commercially available AAT compositions can be used to treat a subject described herein.

In some embodiments, compositions can be administered to a subject based on time course and extent of cardiac remodeling, including the severity of the insult, secondary events (recurrent ischemia or infarction), neurohormonal activation, and genetic factors and gene expression. In some embodiments, compositions disclosed herein can be administered to a subject before, during or after a cardiac event. In other embodiments, compositions disclosed herein can be administered to a subject within 48 hours of an event (e.g. about 24 hours after the cardiac event). In certain embodiments, compositions disclosed herein can be administered to a subject several days to weeks after a cardiac event, for example 5 days, 7 days, 2 weeks or more. It is contemplated that a subject having a cardiac event can be treated continuously or at pre-determined intervals to prevent remodeling.

Some embodiments can concern combination therapies for reducing the adverse effects of a cardiac event that include any composition disclosed herein, alone or in combination with other agents. For example, combination therapies may include other therapeutic formulations that may attenuate remodeling. For example, angiotensin-converting enzyme (ACE) inhibitors may decrease remodeling or transmural infarction and chronic pressure overload. Alternatively inhibition of aldosterone, either directly or indirectly, may to improvement in remodeling. Early correction of congenital heart defects, if appropriate, may modulate remodeling, as well as treatment of chronic hypertension or valvular heart disease.

In other embodiments, a composition may further include, but is not limited to, an anti-inflammatory agent, an immunosuppressive agent, an immunomodulatory agent, an anti-microbial agent, an anti-viral agent, an anti-bacterial agent, other known cardiac treatment agents and a combination thereof.

Other embodiments herein concern methods of treating a subject having or suspected of having a cardiac event including administering to the subject in need of such a treatment a therapeutically effective amount of a composition including but not limited alpha-1 antitrypsin, a fragment thereof, an analog thereof, a fusion molecule thereof, or a mutant molecule thereof having no significant serine protease inhibition activity. Further, administration of the composition to the subject can be before, during, or after a cardiac event or combination thereof.

In accordance with these embodiments, a cardiac event can be a myocardial infarction, myocardial ischemia, chronic systemic arterial and venous hypertension and pulmonary arterial and venous hypertension, congenital heart disease with and without intracardiac shunting, valvular heart disease, idiopathic dilated cardiomyopathy, infectious and non-infectious myocarditis, endocarditis or pericarditis, stress cardiomyopathy (as seen associated with critical care illnesses, physical and emotional stress, and intracranial hemorrhage and stroke) and septic cardiomyopathy, atrial and ventricular arrhythmias, cardioplegia, cardiac arrest or other event that damages heart muscle.

In certain embodiments, a subject may be administered one or more infusions of any composition disclosed herein, for example, one or more of, AAT, AAT-mutant or AAT carboxyterminal-derived peptide composition to modulate cardiac remodeling in a subject having a cardiac condition. In certain examples, the subject may have suffered a recent cardiac event or suffered a cardiac event a week ago, or a month ago, or a year or more prior to administration of the AAT composition. In other examples, the subject may have suffered from previous cardiac events and is suspected of having another event.

In other embodiments, compositions disclosed herein can be used to treat a subject having had a cardiac event wherein the cardiac event is complicated by excess production of caspase-1. These treatments can be used to reduce cardiac remodeling and/or reduce death of cardiac cells or tissues at early stages middle stages or late stages of remodeling after the cardiac event.

In certain embodiments, compositions of AAT or AAT-derived carboxyterminal peptides capable of binding to SEC receptors or compositions with AAT-like activities may be administered to a subject in need thereof to reduce cardiac remodeling in the subject compared to a control not administered such a composition. As disclosed herein the carboxy terminal region of AAT includes the last 80 amino acids of SEQ ID NO:1 or human AAT molecule or other naturally occurring AAT molecule. In other embodiments, peptides derived from AAT can include 5-mers, 10-mers, 20-mers, 25-mers, 30-mers, 35-mers, 40-mers, 50-mers, and up to an 80 mer of an AAT molecule wherein any of the contemplated peptides have no significant serine protease inhibitor activity, are derived from the carboxyterminus of AAT and are capable of being used for treating a cardiac event.

In one embodiment of the present invention, a composition may include compounds that engage molecules for the SEC receptor to treat a subject. In some of the recited methods, an AAT-mutant or AAT derived peptide (e.g. mammalian derived) having no significant serine protease inhibitor activity contemplated for use within the methods of the present invention can include a series of peptides including carboxyterminal amino acid peptides corresponding to AAT. Among this series of peptides, some include, but are not limited to pentamers or pentameric derivatives of an AAT region, including, but not limited to, FVFLM (SEQ ID NO:2), FVFAM (SEQ ID NO:3), FVALM (SEQ ID NO:4), FVFLA (SEQ ID NO:5), FLVFI (SEQ ID NO:6), FLMII (SEQ ID NO:7), FLFVL (SEQ ID NO:8), FLFVV (SEQ ID NO:9), FLFLI (SEQ ID NO:10), FLFFI (SEQ ID NO:11), FLMFI (SEQ ID NO:12), FMLLI (SEQ ID NO:13), FIIMI (SEQ ID NO:14), FLFCI (SEQ ID NO:15), FLFAV (SEQ ID NO:16), FVYLI (SEQ ID NO:17), FAFLM (SEQ ID NO:18), AVFLM (SEQ ID NO:19), and any combination thereof.

In addition, combinations of amino acid 5-mers or 10-mers or 20-mers or 30-mers or more can also be used. For example, one or more 5-mers or 10-mers or 20-mers etc can include consecutive amino acids starting from AA 315 and ending with AA 394 of naturally occurring AAT represented as SEQ ID NO:1. Other examples contemplated herein can include compositions of SEQ ID NO:2 through SEQ ID NO:38 which may be combined or made into a mixture or made into concatamers and administered to a subject.

As contemplated herein, the later half of a sequence toward the carboxy end is referred to as the carboxyterminus. In certain embodiments, the carboxyl domain of AAT going backwards from the carboxyl terminus is defined as those amino acids most conserved among the difference species and do not participate in the protease binding domain of AAT. In addition, in other embodiments, AAT protease binding domain can be mutated in order to reduce or eliminate the protease function of the molecule and this molecule can be used in any composition contemplated herein. In other embodiments, a mutated molecule can retain its anti-inflammatory effects. Also contemplated herein is that the carboxyl domain is the non-protease binding domain. One skilled in the art would understand a non-protease binding domain of AAT.

In each of the above-recited methods, compositions herein may include peptides derived from the carboxyterminus of AAT. The peptides may include but are not limited to amino acid peptides selected from one or more of LSGVTEEAPL (SEQ ID NO:20); KLSKAVHKAV (SEQ ID NO:21); LTIDEKGTEA (SEQ ID NO:22); AGAMFLEAIP (SEQ ID NO:23); VSIPPEVKFN (SEQ ID NO:32); MSIPPEVKFN (SEQ ID NO:24); KPFVFLMIEQ (SEQ ID NO:25); NTKSPLFMGK (SEQ ID NO:26); VVNPTQK (SEQ ID NO:27), GADLSGVTEE (SEQ ID NO:28); APLKLSKAVH (SEQ ID NO:29); KAVLTIDEKG (SEQ ID NO:30); TEAAGAMFLE (SEQ ID NO:31); RIPVSIPPEV (SEQ ID NO:32); KFNKPFVFLM (SEQ ID NO:33); IEQNTKSPLF (SEQ ID NO:34); MGKVVNPTQK (SEQ ID NO:35); LEAIPMSIPPEVKFNKPFVFLM (SEQ ID NO:36); and LEAIPMSIPPEVKFNKPFVF (SEQ ID NO:37), GADLSGVTEEAPLKLSKAVHKAV LTIDEKGTEAAGAMFLERIPV SIPPEVKFNKPFVFLMIEQNTKSPLFMGKVVNPTQK (SEQ ID NO:38) or any combination thereof. It is contemplated that the AAT-derived peptides from the carboxyterminus recited for use in the compositions and methods herein are also intended to include any and all of those specific AAT peptides other than the 10 amino acid AAT peptides of SEQ ID NO:1 depicted supra. For example, while AAT peptides amino acids 315-324, amino acids 325-334, amino acids 335-344, etc of SEQ ID NO:1 have been enumerated herein, it is intended that the scope of the compositions and methods of use of same specifically include all of the possible combinations of AAT peptides such as amino acids 316-325, amino acid 317-326, 318-327, etc. of SEQ ID NO:1, as well as any and all AAT peptide fragments corresponding to select amino acids of SEQ ID NO:1, without actually reciting each specific AAT peptide of SEQ ID NO:1 therewith. Thus, by way of illustration, and not by way of limitation, Applicants are herein entitled to possession of compositions based upon any and all AAT peptide variants based upon the amino acid sequence depicted in SEQ ID NO:1 and use of such compositions in the methods of the present invention.

In certain embodiments, AAT-associated molecules used in the methods and compositions herein can include, but are not limited to, compositions of SEQ ID NO:1, naturally occurring AAT (394 AA length molecule making up approximately 90% of AAT isolated from serum), or other AAT compositions such as, Aralast™ (Baxter), Zemaira™ (Aventis Behring), Prolastin™ (Bayer), Aprotonin™ or Trasylol™ (Bayer Pharmaceutical Corporation), Ulinistatin™ (Ono Pharmaceuticals, Inc.), and inhalation and/or infectible AAT (Kamada, Ltd., Israel), or any other commercially available AAT compositions or any combination thereof.

In accordance with embodiments of the present invention, the peptide can be protected or derivitized in by any means known in the art for example, N-terminal acylation, C-terminal amidation, cyclization, etc. In a specific embodiment, the N-terminus of the peptide is acetylated.

Other embodiments concern mutants of human AAT where the mutant is generated to have no significant serine protease inhibitor activity. Any method known in the art for generating mutants is contemplated. Some embodiments include using site-directed mutageneis to generate a hATT having no significant serine protease inhibitor activity (see Examples section and pEF-hAAT). Other methods include disrupting the serine protease inhibiting region of hAAT by other disruption methods such as heating hAAT, or generating a mutant (e.g. RCL mutant with a modified cysteine), or chemically modifying hAAT to eliminate or dramatically reduce serine protease inhibitor activity Pharmaceutical Compositions Embodiments herein provide for administration of compositions to subjects in a biologically compatible form suitable for pharmaceutical administration in vivo. By "biologically compatible form suitable for administration in vivo" is meant a form of the active agent (e.g. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

Pharmaceutical compositions containing AAT or peptide fragment thereof, or analog thereof, or mutant thereof, or a functional derivative thereof (e.g. pharmaceutical chemical, protein, peptide of some of the embodiments) may be administered to a subject, for example by subcutaneous, intravenous, intracardiac, intracoronary, intramuscular, by oral administration, by inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the composition may be administered intranasally, such as inhalation.

Some embodiments disclosed herein concern using a stent or a catheter to deliver one or more agents (e.g. compositions disclosed herein) to a subject having or suspected of having a cardiac event. Any stent or other delivery method known in the art that can deliver one or more agents directly to cardiac tissue is contemplated. These delivery techniques can be used alone or in combination with other delivery methods.

A compound (e.g. a peptide, protein or mixture thereof) may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art. Solutions of the active compounds as free-base or pharmacologically acceptable salts can be prepared in water suitably mixed with a surfactant, such as hydroxypropylcellulose.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition such as daily, bi-weekly, weekly, bi-monthly etc. Pharmaceutical compositions are administered in an amount, and with a frequency, that is effective to modulate cardiac remodeling. The precise dosage and duration of treatment may be determined empirically using known testing protocols or by testing the compositions in model systems known in the art and extrapolating therefrom. Dosages may also vary with the severity of the condition. In certain embodiments, the composition range can be between 10 and 75 mg/kg introduced daily or weekly to a subject. A therapeutically effective amount of α1-antitrypsin, peptides, or drugs that have similar activities as α1-antitrypsin or peptides can be also measured in molar concentrations and can range between about 1 nM to about 2 mM.

In another embodiment, nasal solutions or sprays, aerosols or inhalants may be used to deliver the compound of interest. Additional formulations that are suitable for other modes of administration may include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Liposomes or microparticles can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In some embodiments, compositions and methods concern a compound having no significant serine protease inhibitor activity but having other α1-antitrypsin activity or analog thereof may be used in a single therapeutic dose, acute manner or a chronic manner to treat cardiac episodes or prolonged cardiac conditions, respectively, for example in reducing or eliminating cardiac remodeling.

In certain embodiments of the methods of the present invention, the subject may be a mammal such as a human or a captive or a domesticated animal or pet.

Desirable blood levels of compositions disclosed herein may be maintained by continuous infusion to provide about 0.01-5.0 mg/kg/hr or by intermittent infusions containing about 0.4-20 mg/kg of the active ingredient(s). Buffers, preservatives, antioxidants and the like can be incorporated as required. It is intended herein that the ranges recited also include all those specific percentage amounts between the recited range. For example, the range of about 0.4 to 20 mg/kg also encompasses 0.5 to 19.9%, 0.6 to 19.8%, etc, without actually reciting each specific range therewith.

Commercially available agents already approved for different use in humans will work as a treatment for modulating cardiac remodeling in a subject. Some of these agents are currently used for indications other than modulating cardiac remodeling, and may include injectible AAT, plasma preparations, aprotinin and others (American J. of Resp Critical Care Med 1998, Vll 158: 49-59, incorporated herein by reference in its entirety). In one embodiment, compositions contemplated herein may be delivered by inhalation. This mode of focused drug delivery may augment serine protease inhibitor activity within the lung tissues and associated lymphatics to quickly deliver it to cardiac tissue for effect.

Isolated Proteins

One aspect of the invention pertains to proteins, and peptide derivatives thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques and then the serine protease inhibitor activity can be dramatically reduced or eliminated. In another embodiment, polypeptides can be produced by recombinant DNA techniques. Alternative to recombinant expression, polypeptides can be synthesized chemically using standard peptide synthesis techniques.

One embodiment pertains to isolated proteins, and biologically active peptides thereof. In one embodiment, the native polypeptide can be isolated from cells or tissue sources by an appropriate purification scheme using standard protein purification techniques. In certain embodiments, the native polypeptide may be heated or otherwise treated to reduce or eliminate serine protease inhibitor activity. In certain particular embodiments, serine protease inhibitor activity is reduced where no significant activity remains. In another embodiment, polypeptides contemplated herein are produced by recombinant DNA techniques. Alternative to recombinant expression, a polypeptide can be synthesized chemically using standard peptide synthesis techniques. Any of the peptide or protein molecules contemplated of use in compositions disclosed herein can be compositions having no significant serine protease inhibitor activity. For example, AAT compositions may be treated in order to reduce or eliminate serine protease inhibitor activity or an AAT polypeptide may be isolated wherein the polypeptide has reduced or no significant serine protease inhibitor activity.

An "isolated" or "purified" protein or biologically active portion thereof is substantially free of cellular material or other contaminating proteins from the cell or tissue source from which the protein is derived, or substantially free of chemical precursors or other chemicals when chemically synthesized. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

In certain embodiments, polypeptides can include a polypeptide having a consecutive amino acid sequence corresponding to a portion or all of the last 80 amino acids of carboxyterminus of AAT or AAT allele. Other useful proteins are substantially identical to any portion of the carboxyterminus, and retain the functional activity of the peptide of the corresponding naturally-occurring protein other than serine protease inhibitor activity yet differ in amino acid sequence due to natural allelic variation or mutagenesis.

Some compositions disclosed herein may be used as therapeutic agents in the treatment of a physiological condition caused in whole or part, by excessive serine protease activity. In addition, a physiological condition can be inhibited in whole or part. Peptides contemplated herein may be administered in a composition as free peptides or pharmaceutically acceptable salts thereof. Peptides may be administered to a subject as a pharmaceutical composition, which, in most cases, will include the peptide and/or pharmaceutical salts thereof with a pharmaceutically acceptable carrier.

Biologically active portions of a polypeptide of the invention include polypeptides including amino acid sequences sufficiently identical to or derived from the amino acid sequence of the protein (e.g., the amino acid sequence shown in any of SEQ ID NOs:2 to 38, which exhibit at least one activity of the corresponding full-length protein). A biologically active portion of a protein of the invention can be a polypeptide, which is, for example, 5, 10, 20, 30, 40 or more amino acids in length. Moreover, other biologically active portions having no significant serine protease inhibitor activity, in which other regions of the protein are deleted, can be prepared by recombinant techniques and evaluated for one or more of the functional activities of the native form of a polypeptide disclosed herein.

In certain embodiments, polypeptides may have the amino acid sequence of SEQ ID NOs:1 to 38. Other useful proteins are substantially identical (e.g., at least about 45%, preferably 55%, 65%, 75%, 85%, 95%, or 99%) to any of SEQ ID NOs:1 to 38.

Variants of AAT molecules having no significant serine protease activity can be generated by mutagenesis, e.g., discrete point mutation or truncation. For example, a point mutation may be generated in AAT or peptide derivative thereof that still leaves the reactive center loop intact (RCL)

while interfering with or preventing serine protease binding capabilities with the AAT or peptide but retaining its ability to modulate cardiac remodeling. An agonist can retain substantially the same, or a subset, of the biological activities of the naturally occurring form of the protein except no significant serine protease activity remains. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Fusion Polypeptides

In other embodiments, agents such as AAT and/or analog thereof, or peptide derivative thereof may be part of a fusion polypeptide. In one example, a fusion polypeptide may include AAT (e.g. naturally occurring mammalian α1-antitrypsin) or an analog thereof and a different amino acid sequence that may be heterologous to AAT or analog substance. In addition, a fusion polypeptide disclosed herein can include a pharmaceutically acceptable carrier, excipient or diluent. Any known methods for generating a fusion protein or fusion peptide are contemplated herein.

In yet another embodiment, AAT polypeptide or peptide fusion protein can be a GST fusion protein in which is fused to the C-terminus of GST sequences. Fusion expression vectors and purification and detection means are known in the art. Expression vectors can routinely be designed for expression of a fusion polypeptide of the invention in prokaryotic (e.g., $E.$ $coli$) or eukaryotic cells (e.g., insect cells (using baculovirus expression vectors), yeast cells or mammalian cells) by means known in the art. In yet another embodiment, a nucleic acid of the invention is expressed in mammalian cells using a mammalian expression vector as described in the art.

Combination Therapies

Any of the embodiments detailed herein may further include one or more a therapeutically effective amount of cardiac-related medications (e.g. to treat myocardial infarction or other condition disclosed herein). These therapies can include, but are not limited to, aspirin and other antiplatelet therapy including for example, clopidogrel, prasugrel, ticagrelor, abciximab, eptifibatide, tirofiban; heparin and derivatives; direct thrombin inhibitors or Xa inhibitors; warfarin; angiotensin converting enzyme inhibitors or angiotensin receptor blockers; beta- and alpha-adrenergic receptor blockers; calcium channel blockers; HMGCoA reductase inhibitors (e.g. statins); niacin and derivatives; fenofibrate; fish oil; aldosterone blockers; hydralazine and nitroderivates; phosphodiesterase inhibitors; direct guanylil cyclase activators, anti-microbial drugs, anti-inflammatory agent, immunomodulatory agent, or immunosuppressive agent or combination thereof.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, keto-conazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents contemplated of use herein can include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole, (sulfamethoxazole/trimethoprim), and pentamidine isethionate.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents which treat the immune, vascular, or lymphatic systems or any combination thereof.

Anti-inflammatory or immunomodulatory drugs or agents contemplated of use herein can include, but are not limited to, interferon derivatives, e.g., betaseron, β-interferon; prostane derivatives, iloprost, cicaprost; glucocorticoids such as cortisol, prednisolone, methylprednisolone, dexamethasone; immunsuppressive agents such as cyclosporine A, FK-506, methoxsalen, thalidomide, sulfasalazine, azathioprine, methotrexate; lipoxygenase inhibitors, e.g., zileutone, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukines, other cytokines, T-cell-proteins; antibodies against receptors of interleukins, other cytokines, and T-cell-proteins.

Other agents of use in combination with compositions herein can be molecules having serine protease inhibitor activity. For example other serine protease inhibitors contemplated of use herein can include, but are not limited to, leukocyte elastase, thrombin, cathepsin G, chymotrypsin, plasminogen activators, and plasmin.

In addition, other combination compositions of methods disclosed herein can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. In certain embodiments, antibody-based therapies may be used as induction therapy in combination with the compositions and methods disclosed herein.

Subjects contemplated herein can include human subjects, or other subjects such as non-human subjects, including but not limited to, primates, dogs, cats, horses, cows, pigs, guinea pigs, birds and rodents.

AAT

Human AAT is a single polypeptide chain with no internal disulfide bonds and only a single cysteine residue normally intermolecularly disulfide-linked to either cysteine or glutathione. One reactive site of AAT contains a methionine residue, which is labile to oxidation upon exposure to tobacco smoke or other oxidizing pollutants. Such oxidation reduces the elastase-inhibiting activity of AAT; therefore substitution of another amino acid at that position, e.g., alanine, valine, glycine, phenylalanine, arginine or lysine, produces a form of AAT which is more stable. Native AAT can be represented by the following formula:

(SEQ ID NO: 1)
EDPQGDAAQKTDTSHHDQDHPTFNKITPNLAEFAFSLYRQLAHQSNSTN

IFFSPVSIATAFAMLSLGTKADTHDEILEGLNFNLTEIPEAQIHEGFQE

LLRTLNQPDSQLQLTTGNGLFLSEGLKLVDKFLEDVKKLYHSEAFTVNF

GDTEEAKKQINDYVEKGTQGKIVDLVKELDRDTVFALVNYIFFKGKWER

PFEVKDTEEEDFHVDQVTTVKVPMMKRLGM FNIQHCKKLSSWVLLMKY

LGNATAIFFLPDEGKLQHLENELTHDIITKFLENEDRRSASLHLPKLSI

TGTYDLKSVLGQLGITKVFSNGADLSGVTEEAPLKLSKAVHKAVLTIDE

KGTEAAGAMFLEAIPMSIPPEVKFNKPFVFLMIEQNTKSPLFMGKVVNP

TQK.

Kits

In still further embodiments, kits for use with the methods described above are contemplated. Kits may include AAT, one or more peptides derived from AAT, a mutant AAT composition, a mutant AAT molecule associated with a gene therapy delivery system or other combinations. Small molecules, proteins or peptides may be employed for use in any of the disclosed methods. In addition, other agents such as anti-bacterial agents, immunosuppressive agents, anti-inflammatory agents may be provided in the kit. The kits can include, suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means or other delivery device (e.g. a stent or catheter). A kit will also generally contain a second, third or other additional container into which other combination agents may be placed. Such containers may include injection or blow-molded plastic containers into which the desired vials are retained.

In certain embodiments, a kit can include a composition including, but not limited to, AAT, AAT fragment, or an AAT analog or polypeptide, having no significant serine protease inhibitor activity. In accordance with these embodiments, a kit can contain AAT or an analog thereof having no significant serine protease inhibitor activity.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the some embodiments which are disclosed and still obtain a like or similar result without departing from the spirit and scope of the invention.

Methods

Experimental Acute Myocardial Infarction (AMI) Model

Adult male out-bred ICR (CD1) mice were used, supplied by Harlan Sprague Dawley (Indianapolis, Ind.). Mice were orotracheally intubated under anesthesia (pentobarbital 50 to 70 mg/Kg), placed in the right lateral decubitus position then subjected to left thoracotomy, pericardiectomy, and ligation of the proximal left coronary artery. Then the ligation was released after 30 min of ischemia, before closure of the thorax. The mice surviving surgery were randomly assigned to the 2 groups of treatment (N=21 per group). Control operations were performed where animals underwent the same surgical procedure without coronary artery ligation (N=8 per group). Two additional groups of mice underwent surgical coronary artery ligation without reperfusion in order to evaluate the effects of AAT in non-reperfused AMI.

After surgery, mice were randomly assigned to treatment with AAT or matching dose of albumin as a control (n=21 per group). Clinical grade human AAT (e.g. Aralast NP®, Baxter, Inc., Thousand Oaks, Calif.), and administered intra-peritoneally at a dose of 60 mg/Kg (approximately 2 mg per mouse in a final volume of 100 µl) immediately after reperfusion, and then daily for 7 days. Human serum albumin (Sigma Aldrich, St. Louis, Mo.) was purchased and administered to mice at an equivalent dose as a control with for the same amount of protein (60 mg/Kg in 100 µl).

Infarct Size Assessment

A subset of mice (N=6 per group) underwent AMI surgery and echocardiogram at 24 hours, followed by immediate sacrifice for measurement of infarct size using triphenyl tetrazolium chloride (TTC) (Sigma Aldrich) staining of viable myocardium. The mouse heart was quickly removed after sacrifice and mounted on a Langendorff apparatus. The coronary arteries were perfused with 0.9% NaCl containing 2.5 mM $CaCl_2$. After the blood was washed out, approximately 2 ml of 1% Evans blue dye (Sigma Aldrich) was injected as a bolus into the aorta until most of the heart turned blue. The heart was then perfused with normal saline solution to wash out the excess Evans blue. Finally, the heart was removed, frozen, and cut into 8-10 transverse slices from apex to base of equal thickness (approximately 1 mm). The slices were then incubated in a 1% TTC isotonic phosphate buffer (pH 7.4) at room temperature for 30 minutes. The areas of infarcted tissue, the risk zone, and the whole LV were determined by computer morphometry using Image Pro Plus 6.0 software (Media Cybernetics, Silver Spring, Md.).

All the remaining mice (N=6 per group) were sacrificed at 7 days and the hearts were explanted and fixed in formalin 10% for at least 48 hours. A transverse section of the median third of the heart was dissected, included in paraffin, cut into 5 µm slides, and stained with Masson's trichrome (Sigma-Aldrich). The areas of fibrosis and the whole left ventricle were determined by computer morphometry using the Image Pro Plus 6.0 software.

Echocardiography

All animals underwent transthoracic echocardiography at baseline (before surgery), at 24 hours and 7 days after surgery (prior to sacrifice). Echocardiography was performed with the Vevo770 imaging system (VisualSonics Inc, Toronto, Ontario, Canada) and a 30-MHz probe measuring left ventricular (LV) end-diastolic diameter (LVEDD), LV end-systolic diameters (LVESD), anterior wall diastolic thickness (AWDT), anterior wall systolic thickness (AWST), posterior wall diastolic thickness (PWDT), and posterior wall systolic thickness (PWST) at M-Mode, according to the American Society of Echocardiography recommendations. LV fractional shortening (FS), ejection fraction (EF), and mass were calculated. The investigator performing and reading the echocardiogram was blinded to the treatment allocation.

Caspase-1 Activity

Caspase-1 activity in clarified homogenates of heart tissue and HL-1 cells was determined by cleavage of a fluorogenic substrate (CaspACE, Promega, Madison, Wis.). The whole heart was explanted 24 hours after surgery and immediately frozen using liquid nitrogen. The samples were homogenized using RIPA buffer (Sigma Aldrich) containing a cocktail of protease inhibitors (Sigma Aldrich) and were centrifuged at 16,000 rpm for 20 minutes. From each sample 75 µg of protein was used for the assay according to the supplier's instructions. Fluorescence was measured after 60 minutes and was expressed as arbitrary fluorescence units produced by one microgram of sample per minute (fluorescence/µg/min) and calculated as fold change compared to sham.

Cardiomyocytes

HL-1 cells are cultured adult cardiomyocytes cultured in Claycomb Medium (Sigma Aldrich) supplemented with 10% FBS. These cells maintain a cardiomyocyte phenotype in vitro. The cells were plated at 1×106 in 60 mm dishes 24 hours before the experiment. Each experiment was performed in triplicate. Prior to the addition of $E.$ $coli$ 0111:B4 LPS (Sigma Aldrich) the medium was replaced with fresh medium containing 8% FBS. AAT or albumin were added at a final concentration of 4 mg/ml. Caspase-1 activation was induced by priming the cells with LPS (25 ng/ml) for 2 hours and then triggered with nigericin (20 µM) or ATP (1-5 mM) for 1 hour. The supernatant media were then removed and the cells frozen until processed as described above. Caspase-3 activity in heart tissue (same samples described above) was measured using the same protocol using a CaspACE kit but with a substrate specific for caspase-3 cleavage.

Leucocyte Infiltrate

The number of infiltrating leucocytes in the infarct area of separate groups of mice was assessed in sham and in albumin-(control) or AAT-treated mice 24 hours after I/R (N=3 per group). Paraffin-embedded tissue slides were stained using hematoxylin and eosin. The leucocytes cells were counted as number of cells per high power field (HPF, ×100) averaged over 5 fields in order to cover the entire infarct area.

Cell Death Assay

HL-1 cells, cultured as described above, were plated at a density of 4×105 in 35 mm dishes. After 24 hours the medium was replaced with 1 ml of fresh medium containing 8% FBS. 4 mg of AAT or human serum albumin were then added. The cells were treated with 25 ng/ml of LPS for 2 hours and then with nigericin (20 µM) or increasing concentrations of ATP (1-5 mM) for 1 hour. After washing, the cells were detached using trypsin (0.05%, GIBCO, Invitrogen) followed by soybean trypsin Inhibitor (GIBCO, Invitrogen), centrifuged at 1500 rpm and resuspended in 1 ml of Claycomb Medium. For each condition, 100 µl of 0.4% Trypan Blue Stain (GIBCO, Invitrogen) was added, mixed and remained at room temperature for 5 minutes. The number of non-viable staining cells was determined in a Thoma chamber and the cell death expressed as percentage of total cells counted. Each experimental condition was performed in triplicate.

Statistics

Differences between the groups were analyzed using the one-way ANOVA and changes in repeated measures in echocardiographic data were analyzed using the random effects ANOVA for repeated-measures to determine the main effect of time, group, and time-by-group interaction. Calculations were completed the SPSS 15.0 package for Windows (SPSS, Chicago, Ill.).

Example 1

Effect of AAT on myocardial ischemia without reperfusion was demonstrated. In one method, transient ligation of the left proximal coronary artery in mice simulates a condition of reperfused AMI in human subjects. Many patients are not adequately reperfused after AMI and these patients are at a high risk for adverse cardiac remodeling. In order to evaluate the effects of AAT in non-reperfused myocardium, model of coronary artery ligation are demonstrated without reperfusion. In this model, there was marked cardiac dilatation with a nearly doubling in LV end-systolic diameter and marked LV systolic dysfunction (with a greater than 50% decrease in LV ejection fraction in albumin-treated mice. In these models, it was demonstrated that AAT treatment significantly reduced the level of LV enlargement (LVESD 3.5±0.3 vs 4.3±0.3 mm, P<0.001) and dysfunction (LVEF 39±1 vs 30±2%, P<0.001) 7 days after AMI without affecting infarct size (28±2% vs 27±3%, P=0.89). This suggests that AAT may promote a more favorable remodeling independently of its infarct-sparing effects.

Caspase-1 Activity in the Ischemic Heart

Figure 4A:
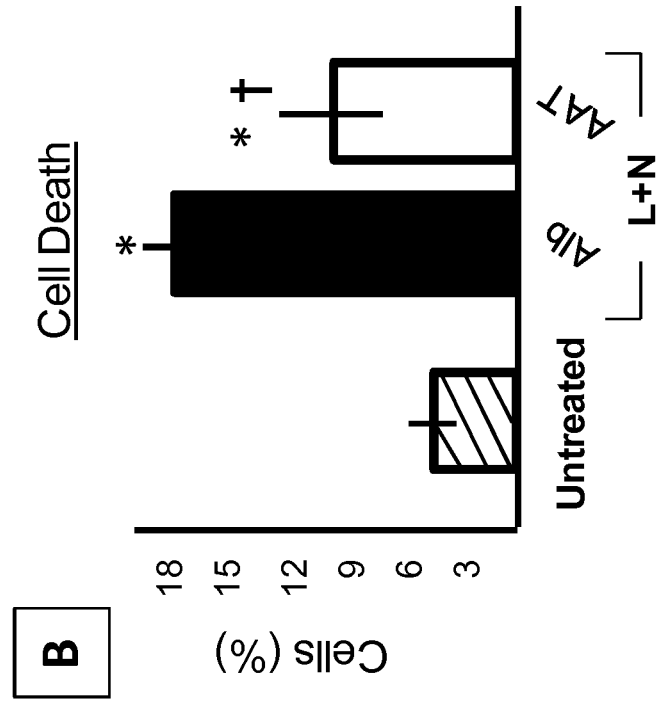
FIGS. 4A-4B represent effects of compositions disclosed herein on certain enzymatic activities (A) and cardiac cell death triggered by activation of caspase-1 (B).

Mice were subjected to transient coronary artery ligation surgery (30 min) or sham surgery and then treated with either AAT or albumin at reperfusion. Hearts were harvested after 24 hours and caspase-1 activity was measured in heart tissue homogenates. As shown in FIG. 4A, in albumin-treated mice caspase-1 activity in the heart increased 3-fold following acute ischemic injury compared to sham operated mice. In sharp contrast, hearts from AAT-treated mice had no significant increase in caspase-1 activity above that in sham-treated mice. Although there was a 50-fold increase in the number of infiltration leukocytes following FR into the peri-infarct area, AAT treatment did not significantly affect this parameter of the response.

Example 2

Then whether there was a preferential effect of AAT on caspase-1 compared to other caspases was evaluated. Therefore, caspase-3 activity was determined in the same heart homogenates. 24 hours after ischemia. Caspase-3 activity in the heart homogenates increased 2-fold in albumin-(control) and AAT-treated mice with a trend toward lower activity with AAT but not reaching statistical significance thus showing a preferential effect of AAT on caspase-1.

The present study demonstrates that in vivo administration of AAT reduces cardiomyocyte. necrosis, decreases infarct size, and prevents cardiac enlargement and dysfunction following experimental AMI. Mice with genetic deletion of caspase-1 have significantly less myocardial damage and more favorable cardiac remodeling after AMI.

These studies demonstrates that treatment with AAT is associated with a marked reduction in caspase-1 activity in the heart resulting in an ameliorative post-AMI phenotype similar to that observed in mice with a complete absence of caspase-1. An inhibitory effect of AAT on caspase-1 activity has been described in a model of renal ischemia-reperfusion injury. In order to determine in the present study whether AAT affects caspase-1 activation directly or indirectly in cardiomyocytes, the effects of AAT on cultured HL-1 adult cardiomyocytes and triggered caspase-1 activation via potassium efflux were examined. The finding of reduced caspase-1 activity in these activated cells in the presence of AAT confirms the related findings in the heart in mice treated with AAT. Moreover, the reduction in caspase-1 activity with AAT paralleled an increase in cell viability. Thus, AAT may directly inhibit the activity of caspase-1 or prevent its activation by inhibiting the upstream events leading to caspase-1 activation. Here, AAT inhibited caspase-1 within a short period of time in cardiomyocytes.

Example 3

In vivo, given at reperfusion during AMI, AAT preserved viable myocardium and limited the initial extent of cell death. Moreover, AAT promoted infarct resorption, a naturally occurring process by which the late infarct size is smaller than the initial damaged area, reflective of an effective clearance of initial edema and inflammatory cells and reduced fibrotic response. Reduction in infarct size led to a more favorable cardiac remodeling as seen with echocardiography 7 days after surgery. Whereas most patients undergo some form of pharmacologic, interventional, or spontaneous reperfusion, a significant number of patients have an incomplete tissue level reperfusion (no reflow), which negates the benefit of reperfusion and is associated with an even greater risk of heart failure. To determine whether the benefits of AAT were limited to reperfused AMI or extended to AMI without reperfusion, AAT was tested in a modified model of AMI in which permanent coronary artery ligation is induced reproducing the most severe clinical scenario of large non-reperfused anterior wall AMI involving approximately 30% of the LV; the findings reported here suggest a benefit in this approach as well. Additionally, the protective effects of AAT were verified in the absence of an effect on infarct size suggesting that AAT promotes a more favorable remodeling independently of its infarct-sparing effects.

Example 4

In another experiment, outcomes in patients with genetic deletion of AAT experience AMI. However, a retrospective observational study had shown that AAT levels increase during AMI to a variable degrees among individual patients, and that those patients with a smaller increase in AAT levels have worse outcomes Purified human AAT is available as a therapeutic agent from different manufacturers and is approved by the Food and Drug Administration for replacement therapy. The 20-year safety profile of purified human AAT, being a natural occurring protein, has led to an expansion of AAT experimental use.

Administration of AAT in mice with experimental AMI suppresses caspase-1 activity, preserves cell viability and promotes more favorable infarct healing, thus preventing adverse cardiac remodeling.

In one exemplary method mice underwent 30 minutes of coronary artery ligation followed by reperfusion and were randomly assigned to receive clinical-grade AAT or albumin at reperfusion. Infarct size was evaluated after 1 (24 hours) and 7 days. Left ventricular (LV) end-diastolic diameter (EDD) and end-systolic diameter (ESD) were measured and LV fractional shortening (FS) and ejection fraction (EF) were calculated using transthoracic echocardiography. Caspase-1 activity was measured in heart tissue 24 hours after surgery. The effect of AAT on caspase-1 activity was also determined in cultured mouse HL-1 cardiomyocytes stimulated with LPS and triggered with either nigericin or ATP.

It was demonstrated that AAT-treated mice had significantly smaller infarct sizes (about 30% at 24 hours and about 55% at day 7) compared with mice treated with albumin. Seven days after acute myocardial infarction (AMI), the AAT-treated mice exhibited a greater than 90% reduced increase in LVEDD and LVESD and reduction in LVEF compared to a control not treated with AAT. In addition, AAT treatment mice resulted in a greater than 90% reduction in caspase-1 activity in heart tissue homogenates 24 hours after ischemia reperfusion and AAT inhibited caspase-1 activity by greater than 80% and prevented necrosis in this mouse model by greater than 50% when added to stimulated cardiomyocytes in vitro. Exogenous administration of AAT reduced caspase-1 activity in the ischemic myocardium leading to preservation of viable myocardium and prevention of adverse cardiac remodeling.

FIGS. 1A-1D represent AAT reduces myocardial necrosis in a model of myocardial ischemia followed by reperfusion in the mouse. FIG. 1A illustrates mean±SEM percent of left ventricle (LV) at risk of infarction (risk area) following FR event. FIG. 1B represents mean±SEM percent of LV infarct size 24 hours following FR event evaluated by triphenyl tetrazolium chloride (TTC) stain. * $p<0.001$ vs sham operated; † $p=0.001$, AAT vs Alb-treated mice. FIGS. 1C-D Triphenyl tetrazolium chloride (TTC) stain of a midventricular heart section from a representative control mouse treated with albumin (C) or AAT (D) 24 hours after the FR event. The infarct area is evident in white/gray within the risk area which appears red/dark pink. The blue area is non-risk area. Alb=albumin. N=6 mice per group.

Figures 2A, 2B, 2C:
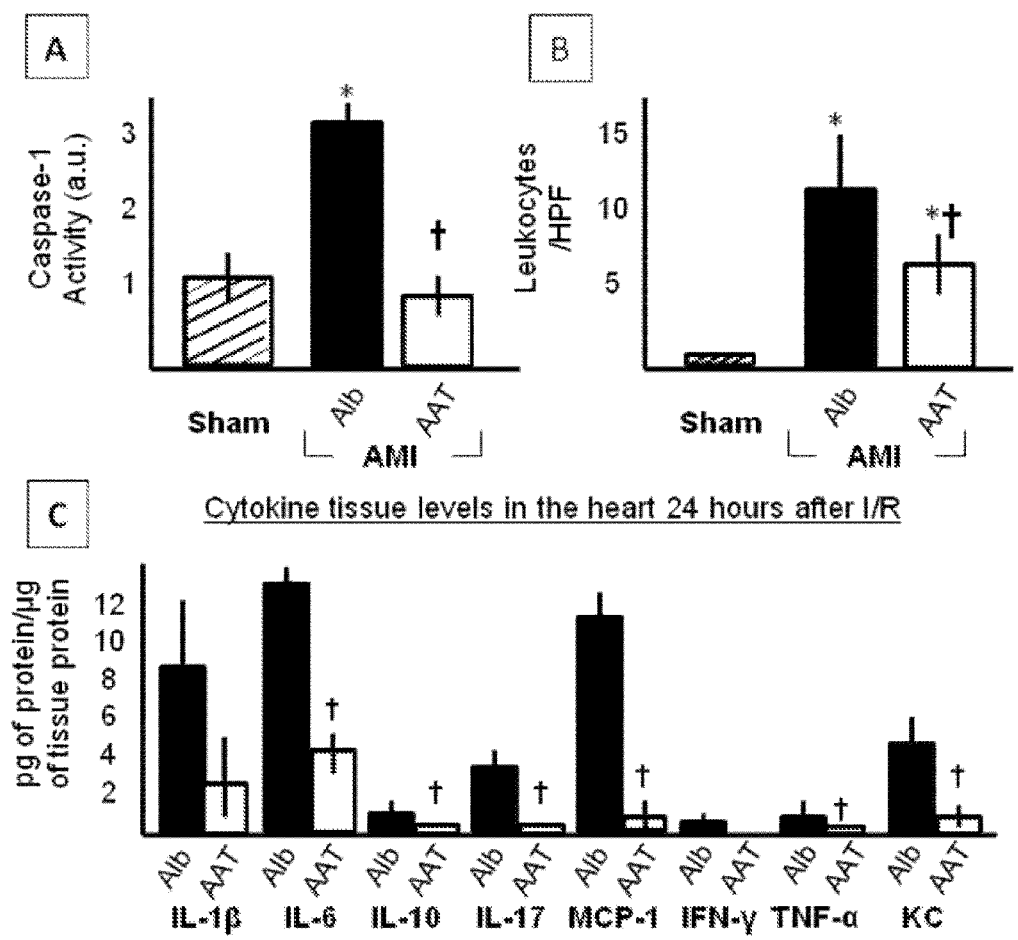
FIGS. 2A-2C represent histogram plots of various studies disclosed herein. (A) represents levels of particular enzymatic activities 24 h after a myocardial event. (B) represents infiltrating leucocytes per high power field (HPF) in the whole LV midventricular section including affected and unaffected areas of the heart. (C) represents cytokine tissue levels after ischemia in the presence or absence of various compositions disclosed herein.

FIGS. 2A-2C represent the effects of AAT on myocardial necrosis in a model of myocardial ischemia followed by reperfusion are mediated by the inhibition of caspase-1 activity, reduced inflammatory response in the heart, and reduced caspase-1-mediated necrosis. (A) represents mean±SEM caspase-1 activity (in arbitrary units) measured 24 h after AMI. * $p<0.001$ vs sham; † $p<0.001$, AAT vs Alb-treated mice (N=6 per group). (B) represents mean±SEM number (×100) infiltrating leucocytes per high power field (HPF) in the whole LV midventricular section including the infarct and non-infarct areas (see Methods). * $p<0.001$, vs sham. AAT-treated mice had significantly less infiltrating leukocyte likely due to a limitation on the infarct size (N=3 per group). (C) represents mean±SEM cytokine tissue levels in the heart 24 hours after ischemia (30 min) and reperfusion in albumin- and AAT-treated mice. † $p<0.001$, AAT vs Alb-treated mice (N=6 per group).

Figures 3A, 3B, 3C:
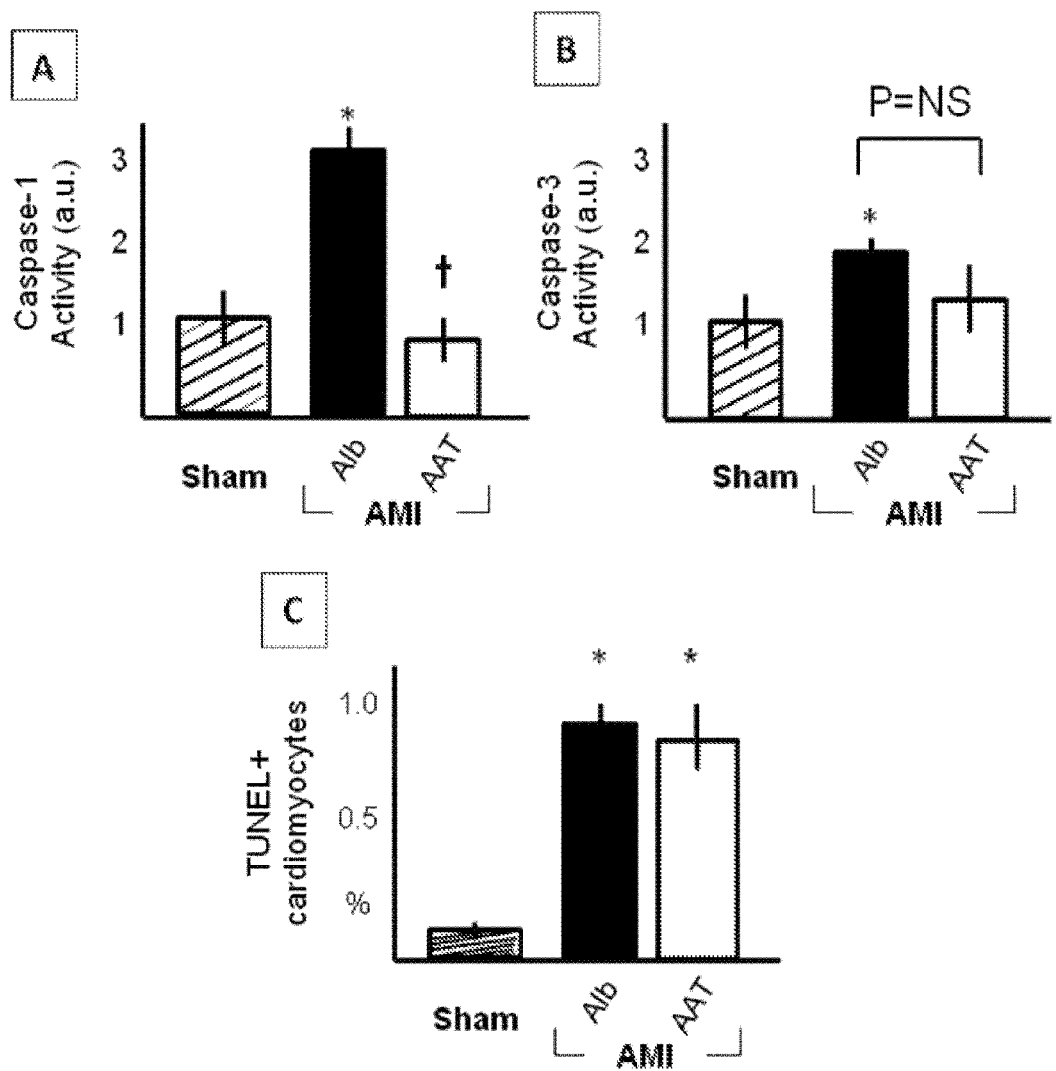
FIGS. 3A-3C represent various experiments analyzing myocardial cell cytokines in the presence and absence of various compositions disclosed herein. (A) represents enzymatic activity independent of the classic apoptosis pathway and (B) represents enzymatic activity related to the apoptosis pathway. (C) represents the presence of certain cardiac cells in the presence or absence of compositions disclosed herein after a cardiac event.

FIGS. 3A-3C represent effects of AAT on myocardial necrosis in a model of myocardial ischemia followed by reperfusion appear to be independent of a reduction in the conventional caspase-3-mediated apoptotic cascade. (A) represents mean±SEM caspase-1 activity (in arbitrary units) measured 24 h after AMI. * $p<0.001$ vs sham; † $p<0.001$, AAT vs Alb-treated mice (N=6 per group). B represents mean±SEM caspase-3 activity (in arbitrary units) measured 24 h after AMI. * $p<0.001$ vs sham; † $p<0.001$, AAT vs Alb-treated mice (N=6 per group). (C) represents mean±SEM number (%) of apoptotic cardiomyocytes defined as TUNEL+/cardiac actine+cells in the infarct area 7 days after ischemia-reperfusion.

Figure 4B:
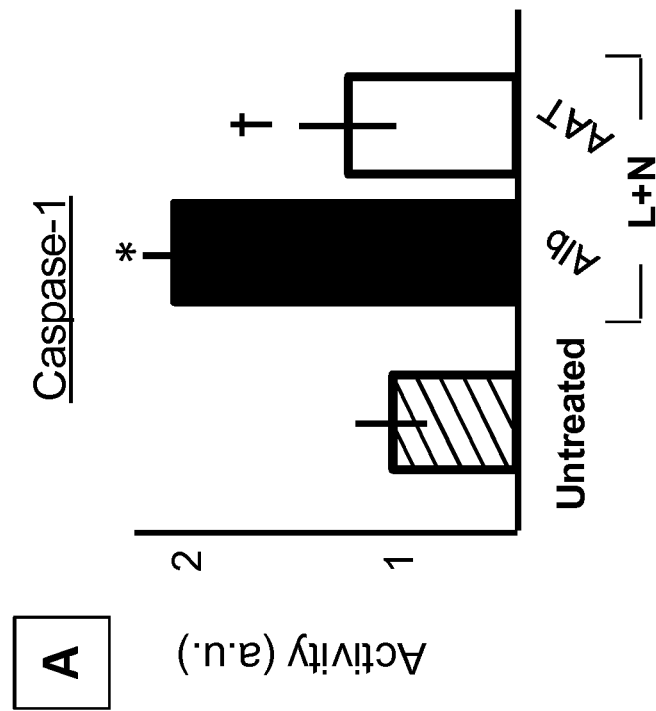

FIGS. 4A-4B represent effects of AAT to inhibit caspase-1 activity and caspase-1-mediated cell death of cardiomyocytes in vitro. A. Mean±SEM caspase-1 activity (in arbitrary units) of HL-1 cells exposed to LPS followed by nigericin (L+N). The concentration of AAT was 4 mg/ml. * p<0.05 vs untreated cells; † p<0.05, AAT vs control, N=3. B. Mean±SEM percent of dead cells. Conditions as above. * p<0.05 vs untreated cells; † p<0.05, AAT vs control, N=3.

Figures 5A, 5B:
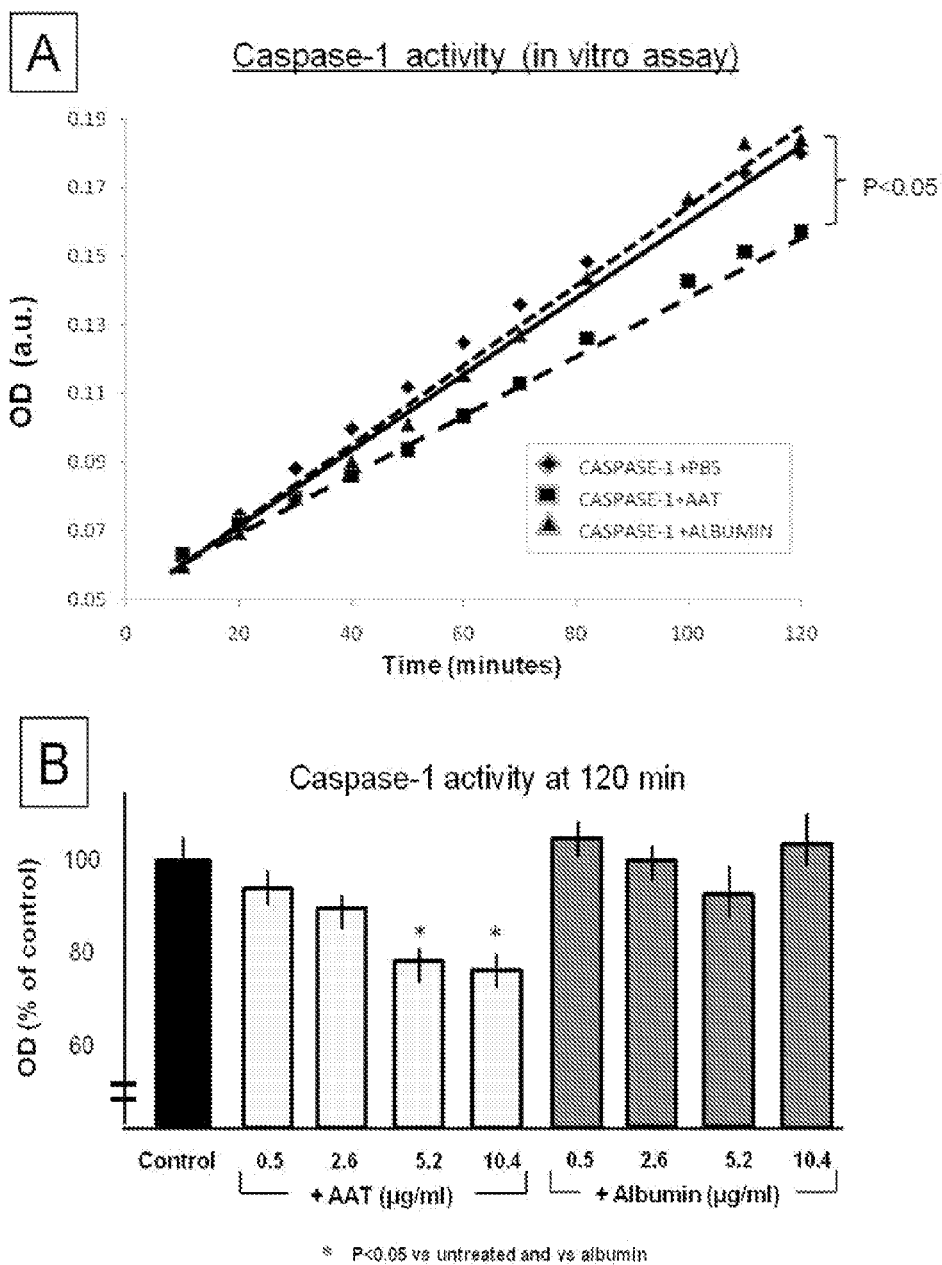
FIGS. 5A-5B represents analysis of compositions disclosed herein and effects on an enzyme of a target pathway

FIGS. 5A-5B represents that AAT has a direct inhibitory effect on caspase-1 activity in vitro. A-B Mean±SEM caspase-1 activity (in arbitrary units) measured at different interval in vitro after incubation of plasma derived AAT or albumin (at increasing concentration), recombinant active caspase-1, and a colorimetric substrate.

Figures 6A, 6B, 6C:
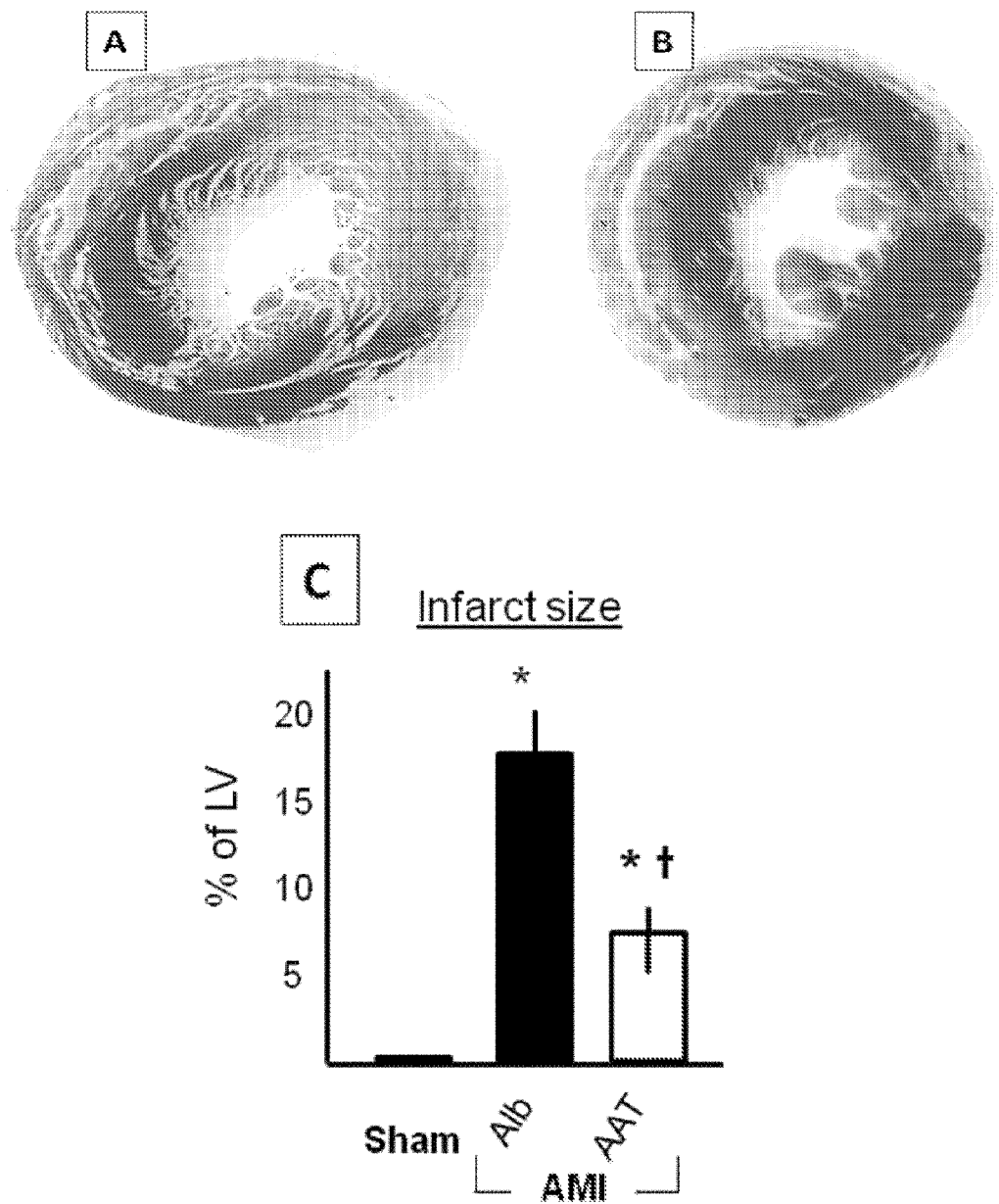
FIGS. 6A-6C represent effects of compositions disclosed herein in a model of myocardial ischemia followed by reperfusion and analysis of effects on scar formation. A-B. Masson's trichrome stain of a midventricular heart section from a representative control mouse treated with various agents 7 days after the ischemia-reperfusion event. (C) represents a histogram reflecting differences in infarct scar size several days after ischemia-reperfusion.
Figures 7A, 7B, 7C, 7D, 7E:
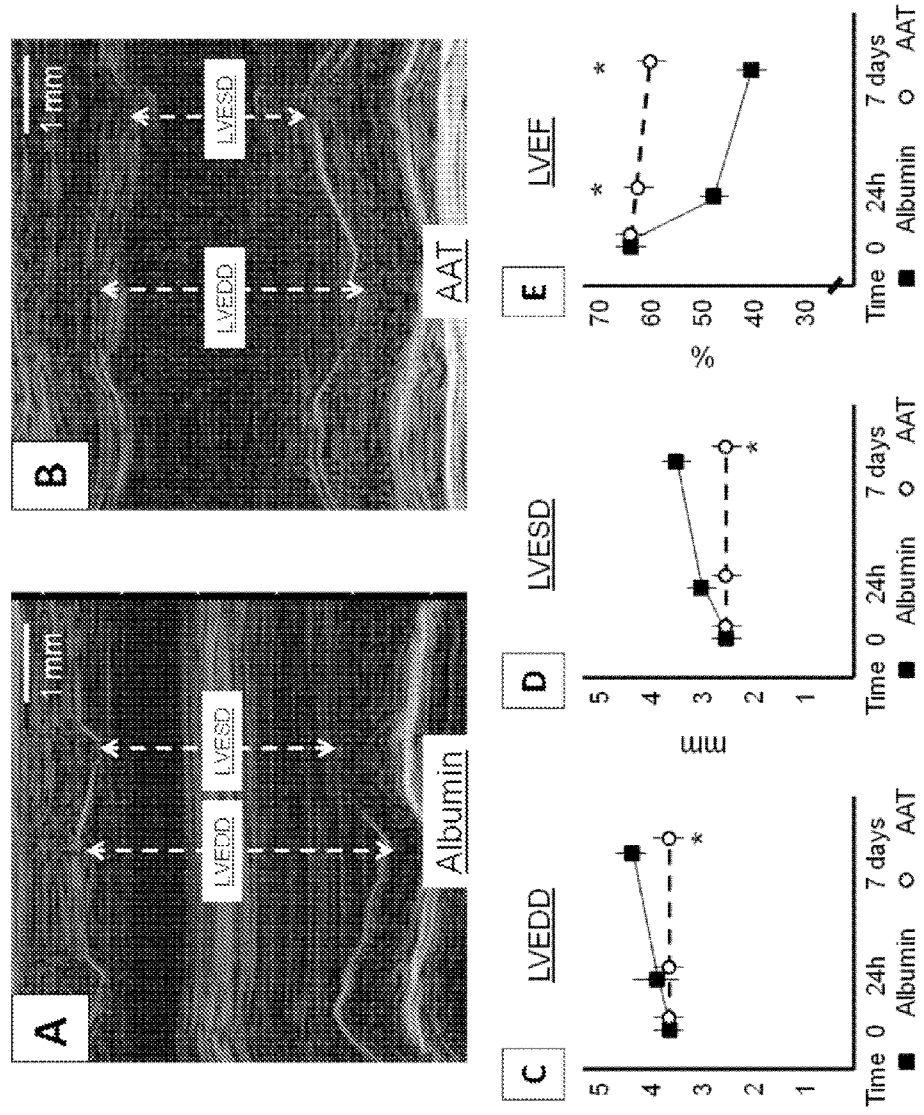
FIGS. 7A-7E represent affect of various agents disclosed herein on cardiac remodeling (e.g. enlargement and dysfunction) several days after ischemia-reperfusion injury in a mouse model.
Figures 8A, 8B, 8C, 8D, 8E:
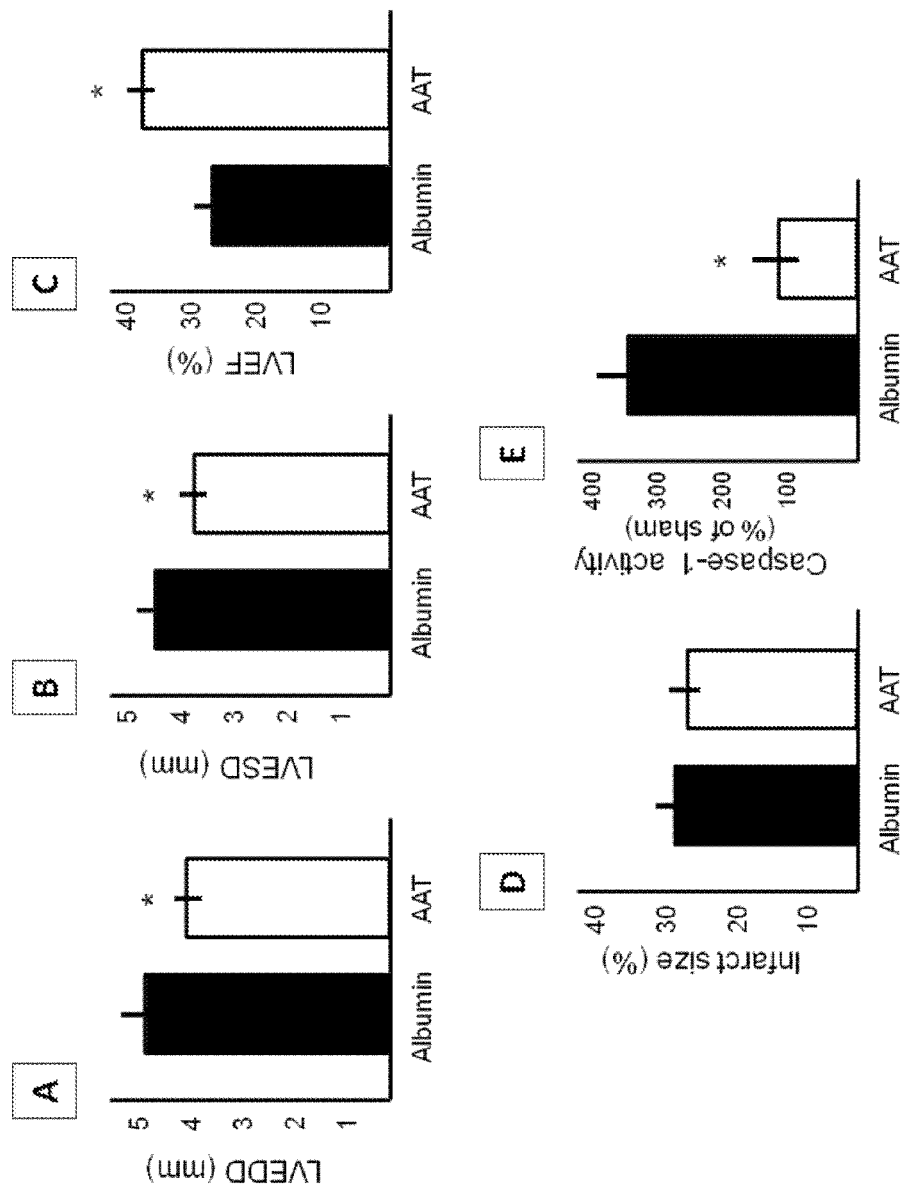
FIGS. 8A-8E represent effects of various compositions disclosed herein on cardiac remodeling (enlargement (A and B) and dysfunction (C)), infarct size (D), and enzymatic activity of a particular enzymatic activity (E) in a mouse model after severe non-reperfused myocardial infarction.
Figures 1A, 1B, 1C, 1D:
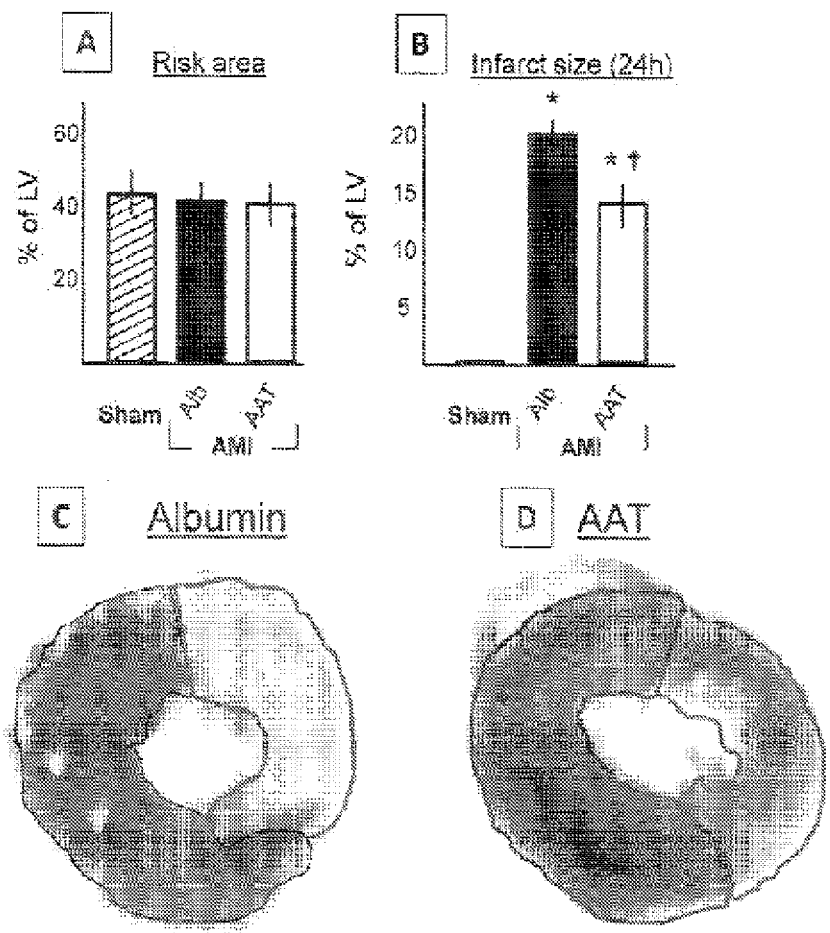
Figures 2A, 2B, 2C:
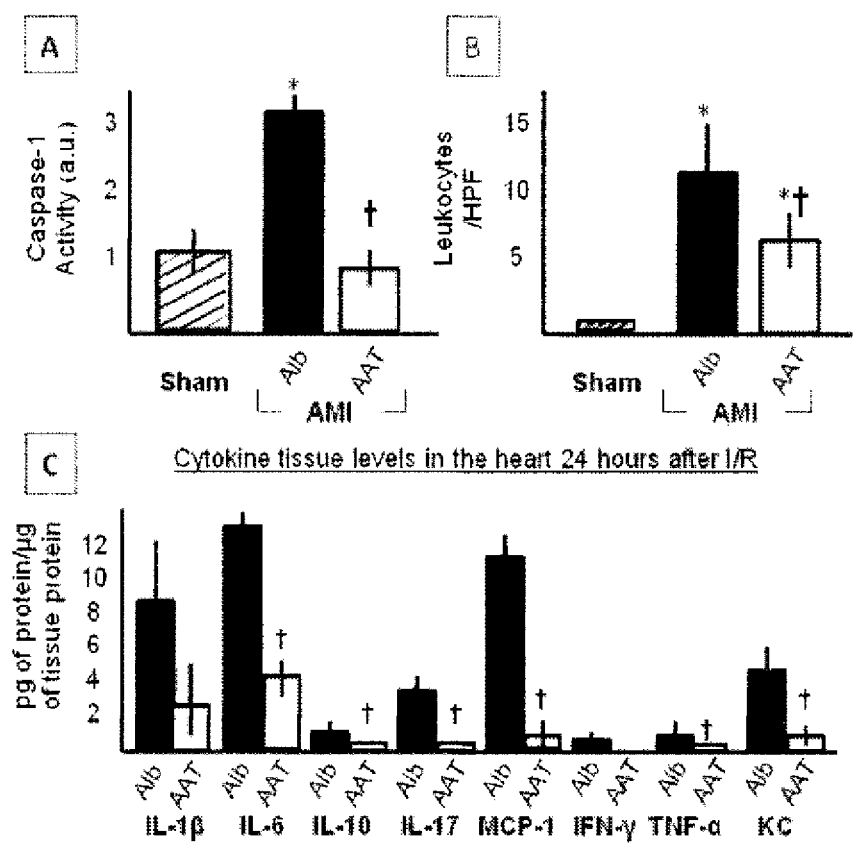
Figures 3A, 3B, 3C:
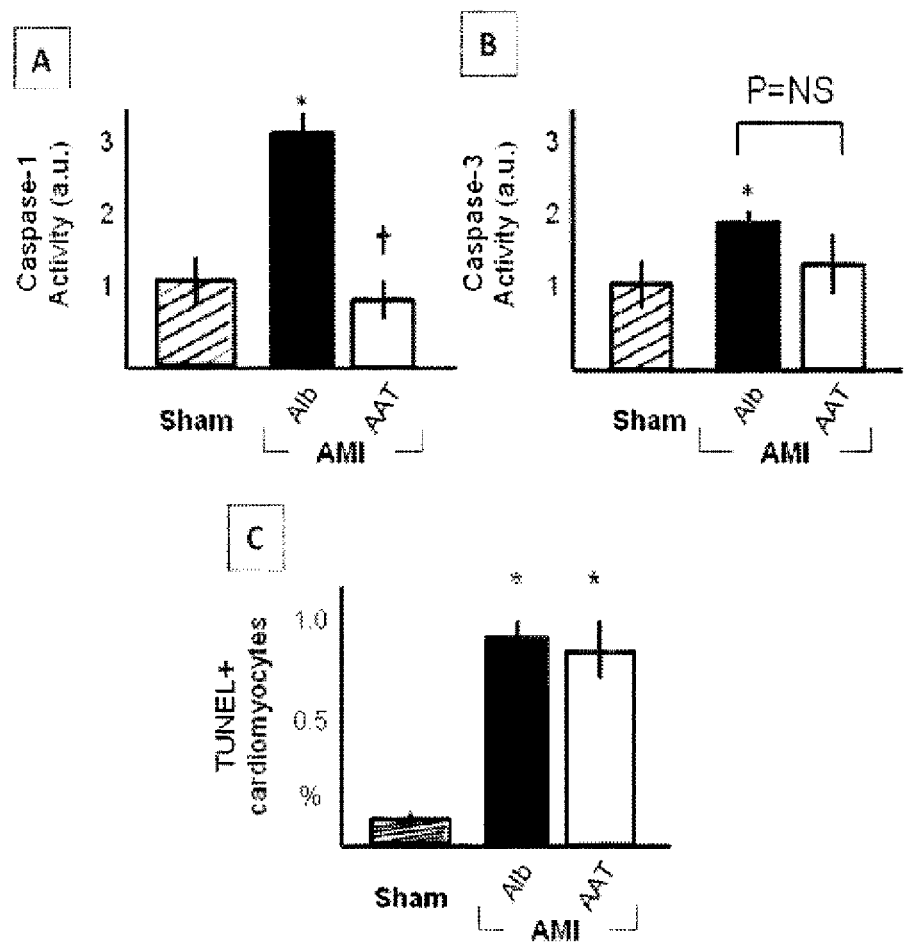
Figures 4A, 4B:
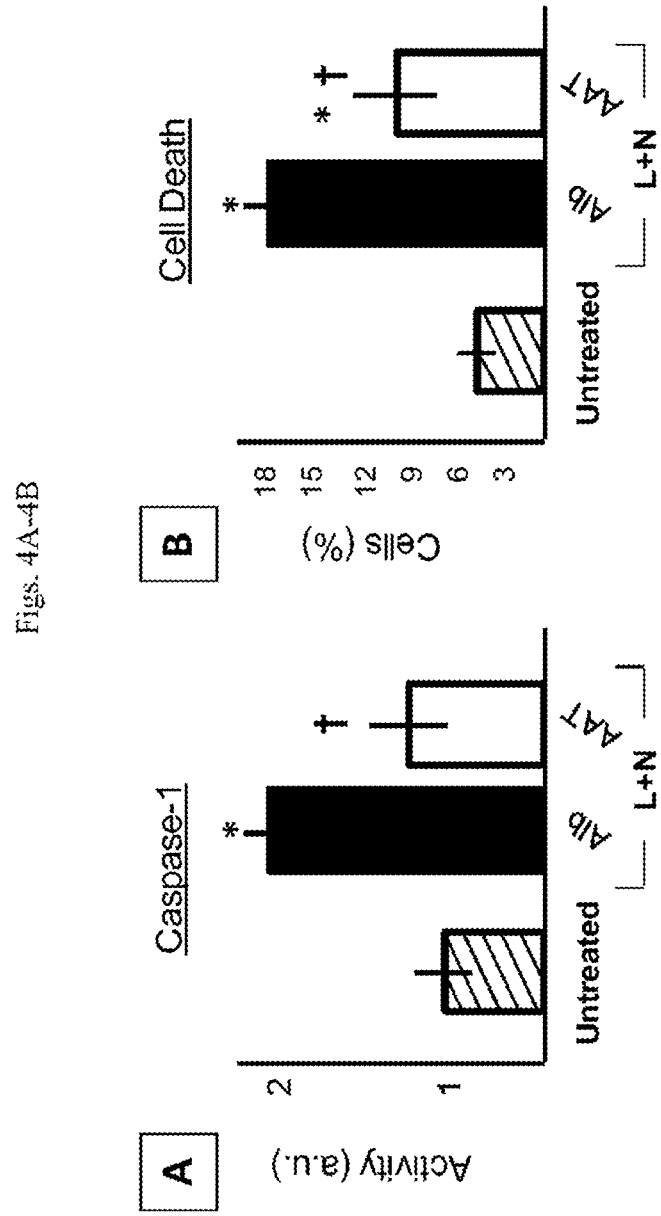
Figures 5A, 5B:
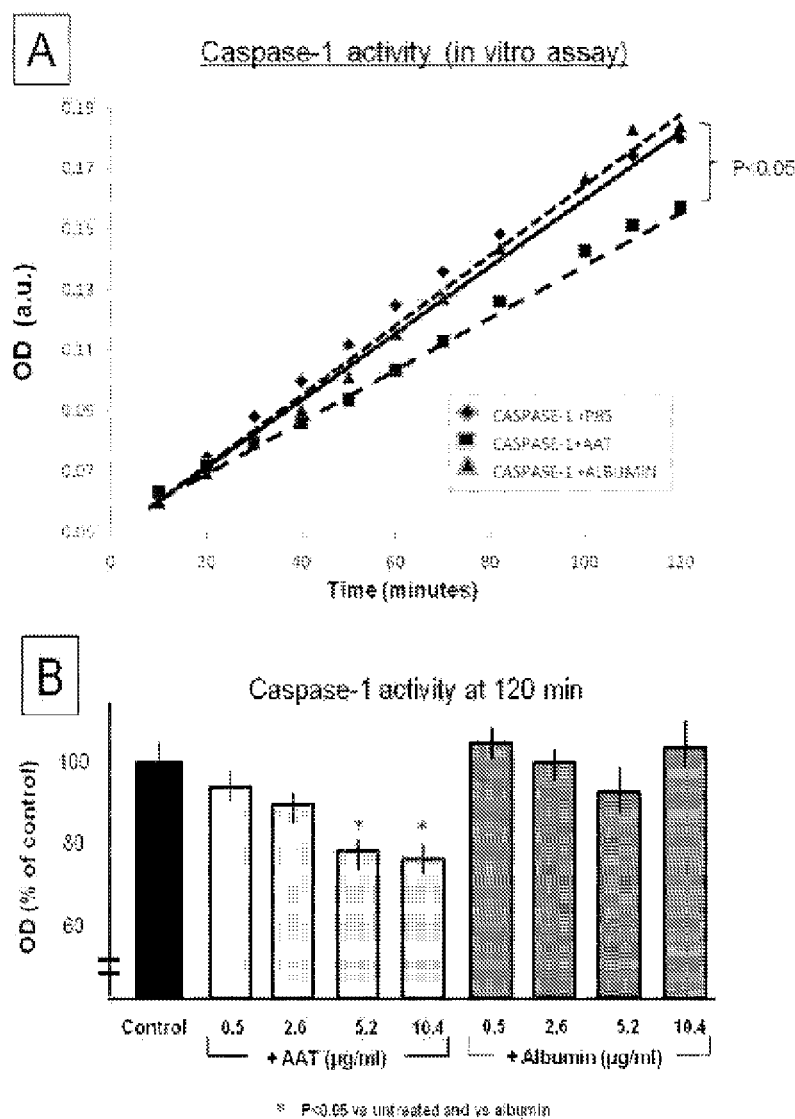
Figures 6A, 6B, 6C:
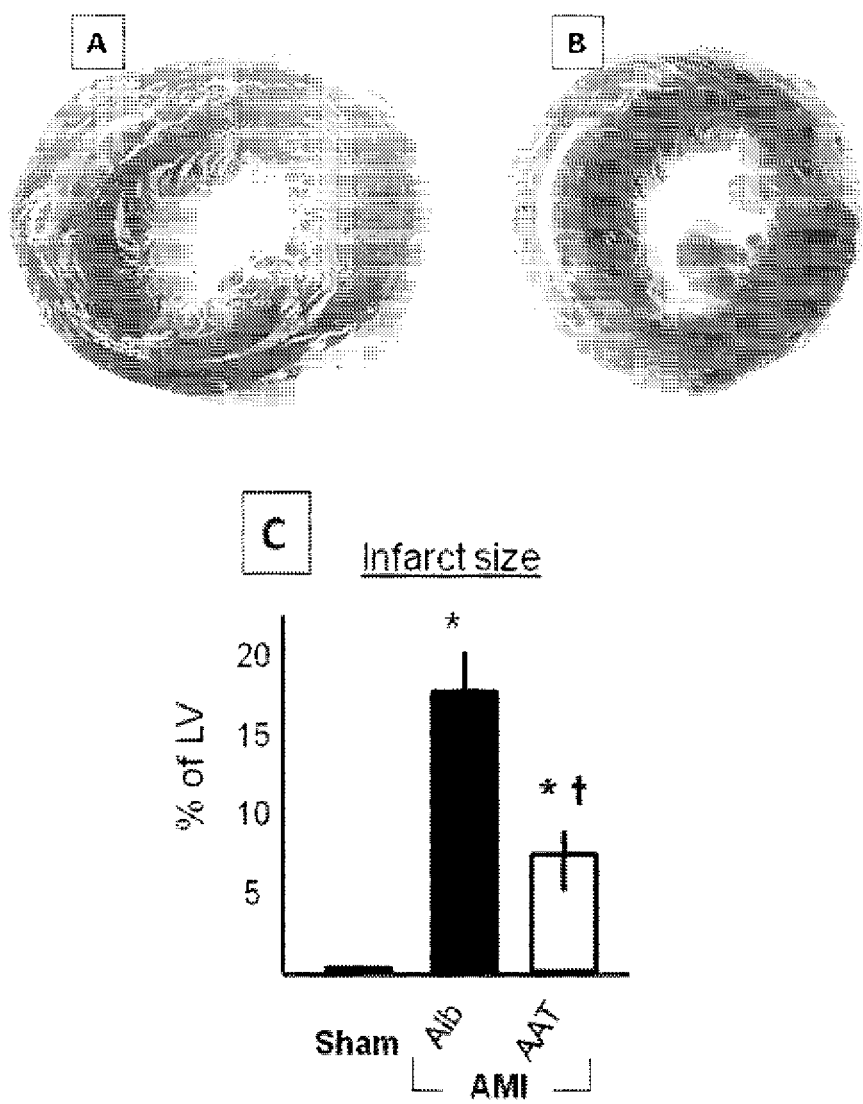
Figures 7A, 7B, 7C, 7D, 7E:
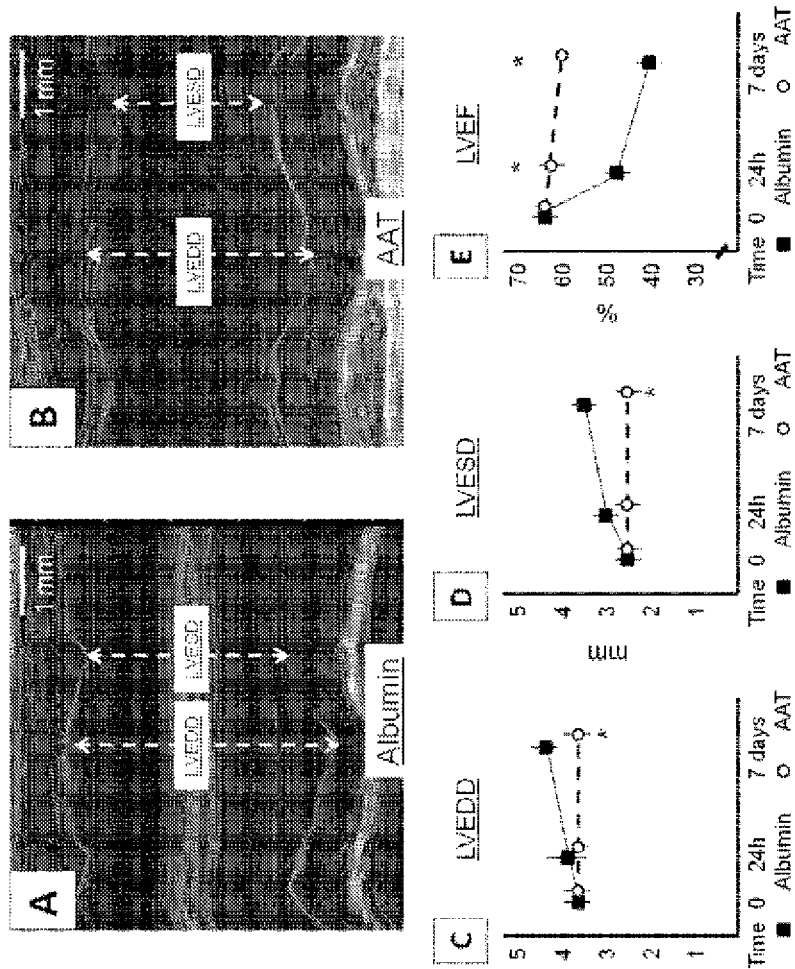
Figures 8A, 8B, 8C, 8D, 8E:
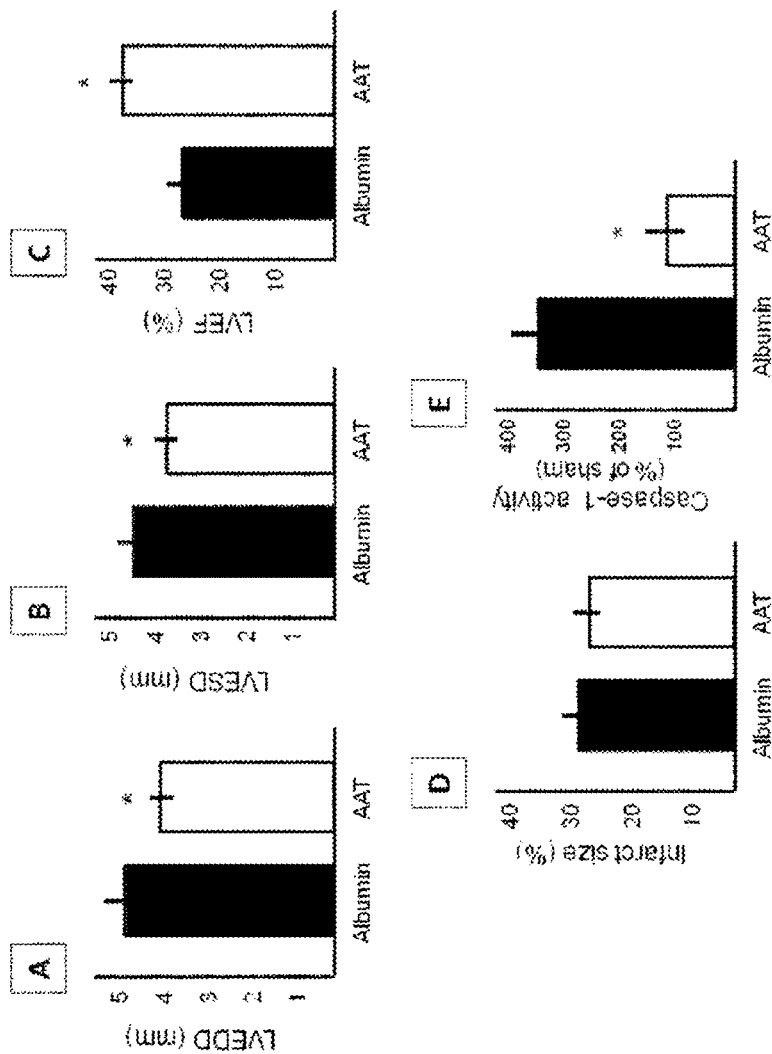

FIGS. 6A-6C represent effects of AAT on necrotic cell death in ischemia-reperfusion in the mouse translate into a smaller infarct scar. A-B represent Masson's trichrome stain of a midventricular heart section from a representative control mouse treated with albumin (D) or AAT (E) 7 days after the FR event. The infarct area is evident in blue/purple. Alb=albumin. N=6 mice per group. C represents mean±SEM percent of LV infarct size 7 days following FR event evaluated by Masson's trichrome stain * p<0.001 vs sham operated; † p=0.001, AAT vs Alb-treated mice.

FIGS. 7A-7E represent the effects of AAT on necrotic cell death in ischemia-reperfusion in the mouse translate into more favorable cardiac remodeling (e.g. reflected in less dilatation and dysfunction). A to B represent M-mode echocardiography recordings of the LV transverse midventricular sections obtained 7 days after AMI in an Alb- (A) and AAT-treated mouse (B). C represents mean±SEM LV end-diastolic diameter (LVEDD), * p=0.0018, AAT vs Alb. D represents mean±SEM LV end-systolic diameter (LVESD), * p=0.001, AAT vs Alb. E represents mean±SEM LV ejection fraction (LVEF), * p=0.007, AAT vs Alb.

FIGS. 8A-8E represent that AAT inhibits caspase-1 activity and ameliorates cardiac remodeling also in a model of severe non-reperfused myocardial infarction, and independent of infarct size sparing. A. Mean±SEM LV end-diastolic diameter (LVEDD), * p<0.001. AAT compared to a control (albumin). B represents mean±SEM LV end-systolic diameter (LVESD), * p<0.001, AAT vs Alb. C represents mean±SEM LV ejection fraction (LVEF), * p<0.001, AAT vs Alb. D. Mean±SEM percent of LV infarct size 7 days following permanent coronary artery ligation (non-reperfused AMI) evaluated by Masson's trichrome stain. The difference between Alb- and AAT-treated mice is not significant (N=6 per group). E. Mean±SEM caspase-1 tissue activity in the heart (in arbitrary units) measured 72 h after non-reperfused AMI. * p<0.001, AAT vs Alb-treated mice (N=6 per group).

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A method for reducing cardiac remodeling in a subject in need thereof comprising:
    administering to the subject having a cardiac condition a composition comprising alpha-1 antitrypsin (AAT), a fragment thereof, a fusion molecule thereof or a mutant thereof, wherein the composition reduces left ventricle end-diastolic diameters (LVEDD) and left ventricle end-systolic diameters (LVESD) in the subject compared to a control subject not receiving the composition; and
    assessing LVEDD and LVESD in the subject within 24 hours of administering the composition to the subject.

2. The method of claim 1, further comprising assessing LVEDD and LVESD at least one additional time following administering the composition to the subject.

3. A method for treating myocardial infarction in a subject in need thereof comprising:
    identifying a subject having a myocardial infarction;
    administering a therapeutically effective amount of a composition comprising one or more of AAT, a fusion molecule thereof, AAT mutant, one or more carboxyterminal peptides derived from AAT to the subject, wherein the composition reduces left ventricle end-diastolic diameters (LVEDD) and left ventricle end-systolic diameters (LVESD) in the subject; and
    assessing LVEDD and LVESD in the subject within 24 hours of administering the composition to the subject.

4. The method of claim 3, further comprising assessing LVEDD and LVESD at least one additional time following administering the composition to the subject.

5. A method for treating a subject suffering from a cardiac event comprising:
    identifying a subject having a cardiac condition;
    assessing the levels of caspase-1 activity in the subject;
    administering a therapeutically effective amount of a composition comprising one or more of AAT, a fusion molecule thereof AAT mutant, one or more carboxyterminal peptides derived from AAT to the subject, wherein the composition reduces left ventricle end-diastolic diameters (LVEDD) and left ventricle end-systolic diameters (LVESD) in the subject; and
    assessing LVEDD and LVESD in the subject within 24 hours of administering the composition to the subject.

6. The method of claim 5, further comprising assessing LVEDD and LVESD at least one additional time following administering the composition to the subject.

7. The method of claim 1, wherein the composition comprises naturally occurring AAT (SEQ ID NO:1).

8. The method of claim 1, wherein the composition comprising alpha-1 antitrypsin (AAT) is a fusion molecule having AAT fused to human IgG or fragment of human IgG.

9. The method of claim 1, wherein the composition comprises a composition of one or more carboxyterminal fragments of naturally occurring AAT.

10. The method of claim 1, wherein the subject is suffering from acute myocardial infarction, myocardial ischemia, chronic systemic arterial and venous hypertension and pulmonary arterial and venous hypertension, congenital heart disease with and without intracardiac shunting, valvular heart disease, idiopathic dilated cardiomyopathy, infectious and non-infectious myocarditis, atrial or ventricular arrhythmias, cardioplegia, cardiac arrest, stress cardiomyopathy, septic cardiomyopathy or other event that damages heart muscle.

11. The method of claim 1, wherein the composition reduces infarct size by at least 10% in the subject compared to the control subject not receiving the composition.

12. The method of claim 3, wherein LVEDD and LVESD are reduced compared to a control subject not receiving the composition.

13. The method of claim 3, wherein the therapeutically effective amount of the composition comprises a single intravenous infusion in the subject of AAT at a dose of about 20 mg/kg to about 150 mg/kg.

14. The method of claim 3, further comprising analyzing blood samples from the subject for levels of active agents after administration.

15. The method of claim 5, wherein the composition is administered to the subject within the first 48 hours of the cardiac event.

16. The method of claim 5, wherein the composition is administered to the subject several days after the cardiac event.

17. The method of claim 5, wherein the cardiac event comprises acute myocardial infarction, myocardial ischemia, chronic systemic arterial and venous hypertension and pulmonary arterial and venous hypertension, congenital heart disease with and without intracardiac shunting, valvular heart disease, idiopathic dilated cardiomyopathy, infectious and non-infectious myocarditis, atrial or ventricular arrhythmias, cardioplegia, cardiac arrest, stress cardiomyopathy, septic cardiomyopathy or other event that damages heart muscle.

18. The method of claim 5, wherein the composition is administered to the subject daily for several days after the event.

19. The method of claim 5, wherein the composition is administered within 24 hours and again several days after the cardiac event.

20. The method of claim 5, wherein caspase-1 is measured before, during or after administration of the composition to the subject.

* * * * *

UNITED STATES PATENT AND TRADEMARK OFFICE
CERTIFICATE OF CORRECTION

PATENT NO. : 9,522,179 B2
APPLICATION NO. : 13/582724
DATED : December 20, 2016
INVENTOR(S) : Dinarello et al.

It is certified that error appears in the above-identified patent and that said Letters Patent is hereby corrected as shown below:

In the Drawings

Delete drawing sheets 1-8, and submit attached drawing sheets 1-8

In the Specification

In Column 2, Line 64, delete "event" and insert -- event. --

In Column 3, Line 16, delete "ventrical" and insert -- ventricle --

In Column 3, Line 17, delete "ventrical" and insert -- ventricle --

In Column 4, Line 41, delete "immunsuppressives" and insert -- immunosuppressives --

In Column 4, Line 42, delete "methoxsalene," and insert -- methoxsalen, --

In Column 4, Line 50, delete "calcipotriols; Celcept®," and insert -- calcipotriol; Cellcept®, --

In Column 6, Line 29, delete "represents" and insert -- represent --

In Column 6, Line 30, delete "pathway" and insert -- pathway. --

In Column 9, Line 22, delete "early stages" and insert -- early stages, --

In Column 9, Line 67, delete "concatamers" and insert -- concatemers --

In Column 10, Line 63, delete "infectible" and insert -- injectable --

Signed and Sealed this
Twenty-second Day of August, 2017

Joseph Matal
*Performing the Functions and Duties of the
Under Secretary of Commerce for Intellectual Property and
Director of the United States Patent and Trademark Office*

In Column 10, Line 67, delete "derivitized" and insert -- derivatized --

In Column 11, Line 8, delete "mutageneis to generate a hATT" and insert -- mutagenesis to generate a hAAT --

In Column 11, Line 15, delete "activity" and insert -- activity. --

In Column 13, Line 32, delete "injectible" and insert -- injectable --

In Column 15, Line 61, delete "quinolonses," and insert -- quinolones, --

In Column 16, Line 5, delete "valgancyclovir," and insert -- valganciclovir, --

In Column 16, Line 6, delete "rimantadin," and insert -- rimantadine, --

In Column 16, Line 6, delete "foscamet," and insert -- foscarnet, --

In Column 16, Line 8, delete "vidarabin," and insert -- vidarabine, --

In Column 16, Line 11, delete "pirethrins/piperonyl butoxide," and insert -- pyrethrins/piperonyl butoxide, --

In Column 17, Line 8, delete "therefore" and insert -- therefore, --

In Column 19, Line 13, delete "(CaspACE," and insert -- (CaspASE, --

In Column 19, Line 42, delete "CaspACE" and insert -- CaspASE --

In Column 20, Line 25, delete "(with" and insert -- with --

In Column 20, Line 45, delete "FR" and insert -- I/R --

In Column 21, Line 53, delete "outcomes Purified" and insert -- outcomes. Purified --

In Column 22, Line 27, delete "FR" and insert -- I/R --

In Column 22, Line 29, delete "FR" and insert -- I/R --

In Column 22, Line 34, delete "FR" and insert -- I/R --

In Column 23, Line 9, delete "represents" and insert -- represent --

CERTIFICATE OF CORRECTION (continued)
U.S. Pat. No. 9,522,179 B2

In Column 23, Line 21, delete "FR" and insert -- I/R --

In Column 23, Line 23, delete "FR" and insert -- I/R --

SEQUENCE LISTING

```
<160> NUMBER OF SEQ ID NOS: 38

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140
```

-continued

```
Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
            165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Phe Val Phe Leu Met
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Phe Val Phe Ala Met
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: synthetic peptide

<400> SEQUENCE: 4

Phe Val Ala Leu Met
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Phe Val Phe Leu Ala
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Phe Leu Val Phe Ile
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Phe Leu Met Ile Ile
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Phe Leu Phe Val Leu
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic peptide

<400> SEQUENCE: 9

Phe Leu Phe Val Val
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: synthetic peptide

<400> SEQUENCE: 10

Phe Leu Phe Leu Ile
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide

<400> SEQUENCE: 11

Phe Leu Phe Phe Ile
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Phe Leu Met Phe Ile
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide

<400> SEQUENCE: 13

Phe Met Leu Leu Ile
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic peptide

<400> SEQUENCE: 14

Phe Ile Ile Met Ile
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic peptide

<400> SEQUENCE: 15

Phe Leu Phe Cys Ile
1               5

<210> SEQ ID NO 16
<211> LENGTH: 5
<212> TYPE: PRT
<213> ORGANISM: Artificial Sequence
<220> FEATURE:
```

<223> OTHER INFORMATION: synthetic peptide

<400> SEQUENCE: 16

Phe Leu Phe Ala Val
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Phe Val Tyr Leu Ile
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide

<400> SEQUENCE: 18

Phe Ala Phe Leu Met
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide

<400> SEQUENCE: 19

Ala Val Phe Leu Met
1               5

<210> SEQ ID NO 20
<211> LENGTH: 10
<212> TYPE: PRT
<213> ORGANISM: Artificial Sequence
<220> FEATURE:
<223> OTHER INFORMATION: synthetic peptide

<400> SEQUENCE: 20

Leu Ser Gly Val Thr Glu Glu Ala Pro Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic peptide

<400> SEQUENCE: 21

Lys Leu Ser Lys Ala Val His Lys Ala Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic peptide

<400> SEQUENCE: 22

Leu Thr Ile Asp Glu Lys Gly Thr Glu Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic peptide

<400> SEQUENCE: 23

Ala Gly Ala Met Phe Leu Glu Ala Ile Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic peptide

<400> SEQUENCE: 24

Met Ser Ile Pro Pro Glu Val Lys Phe Asn
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Lys Pro Phe Val Phe Leu Met Ile Glu Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic peptide

<400> SEQUENCE: 26

Asn Thr Lys Ser Pro Leu Phe Met Gly Lys
1               5                   10

<210> SEQ ID NO 27
<211> LENGTH: 7
<212> TYPE: PRT
<213> ORGANISM: Artificial Sequence
<220> FEATURE:
<223> OTHER INFORMATION: synthetic peptide

<400> SEQUENCE: 27

Val Val Asn Pro Thr Gln Lys
1               5

<210> SEQ ID NO 28
<211> LENGTH: 10
<212> TYPE: PRT
<213> ORGANISM: Artificial Sequence
<220> FEATURE:
<223> OTHER INFORMATION: synthetic peptide

```
<400> SEQUENCE: 28

Gly Ala Asp Leu Ser Gly Val Thr Glu Glu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic peptide

<400> SEQUENCE: 29

Ala Pro Leu Lys Leu Ser Lys Ala Val His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: synthetic peptide

<400> SEQUENCE: 30

Lys Ala Val Leu Thr Ile Asp Glu Lys Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: synthetic peptide

<400> SEQUENCE: 31

Thr Glu Ala Ala Gly Ala Met Phe Leu Glu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: synthetic peptide

<400> SEQUENCE: 32

Arg Ile Pro Val Ser Ile Pro Pro Glu Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic peptide

<400> SEQUENCE: 33

Lys Phe Asn Lys Pro Phe Val Phe Leu Met
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic peptide

<400> SEQUENCE: 34
```

Ile Glu Gln Asn Thr Lys Ser Pro Leu Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthetic peptide

<400> SEQUENCE: 35

Met Gly Lys Val Val Asn Pro Thr Gln Lys
1               5                   10

<210> SEQ ID NO 36
<211> LENGTH: 22
<212> TYPE: PRT
<213> ORGANISM: Artificial Sequence
<220> FEATURE:
<223> OTHER INFORMATION: synthetic peptide

<400> SEQUENCE: 36

Leu Glu Ala Ile Pro Met Ser Ile Pro Pro Glu Val Lys Phe Asn Lys
1               5                   10                  15

Pro Phe Val Phe Leu Met
            20

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

Leu Glu Ala Ile Pro Met Ser Ile Pro Pro Glu Val Lys Phe Asn Lys
1               5                   10                  15

Pro Phe Val Phe
            20

<210> SEQ ID NO 38
<211> LENGTH: 80
<212> TYPE: PRT
<213> ORGANISM: Artificial Sequence
<220> FEATURE:
<223> OTHER INFORMATION: synthetic peptide

<400> SEQUENCE: 38

Gly Ala Asp Leu Ser Gly Val Thr Glu Glu Ala Pro Leu Lys Leu Ser
1               5                   10                  15

Lys Ala Val His Lys Ala Val Leu Thr Ile Asp Glu Lys Gly Thr Glu
            20                  25                  30

Ala Ala Gly Ala Met Phe Leu Glu Arg Ile Pro Val Ser Ile Pro Pro
        35                  40                  45

Glu Val Lys Phe Asn Lys Pro Phe Val Phe Leu Met Ile Glu Gln Asn
    50                  55                  60

Thr Lys Ser Pro Leu Phe Met Gly Lys Val Val Asn Pro Thr Gln Lys
65                  70                  75                  80